US010059712B2

(12) United States Patent  
Yang et al.

(10) Patent No.: US 10,059,712 B2  
(45) Date of Patent: Aug. 28, 2018

(54) N-BENZYL TRYPTANTHRIN DERIVATIVE, AND PREPARATION METHOD AND APPLICATION THEREOF

(71) Applicant: FUDAN UNIVERSITY, Shanghai (CN)

(72) Inventors: Qing Yang, Shanghai (CN); Chunxiang Kuang, Shanghai (CN)

(73) Assignee: Fudan University, Shanghai (CN)

( * ) Notice: Subject to any disclaimer, the term of this patent is extended or adjusted under 35 U.S.C. 154(b) by 0 days.

(21) Appl. No.: 15/036,384

(22) PCT Filed: Nov. 12, 2014

(86) PCT No.: PCT/CN2014/090947  
§ 371 (c)(1),  
(2) Date: May 12, 2016

(87) PCT Pub. No.: WO2015/070766  
PCT Pub. Date: May 21, 2015

(65) Prior Publication Data  
US 2016/0297822 A1   Oct. 13, 2016

(30) Foreign Application Priority Data  
Nov. 12, 2013  (CN) .......................... 2013 1 0560572

(51) Int. Cl.  
*C07D 487/04*  (2006.01)

(52) U.S. Cl.  
CPC ................... *C07D 487/04* (2013.01)

(58) Field of Classification Search  
CPC .................................................. C07D 487/04  
See application file for complete search history.

(56) References Cited

U.S. PATENT DOCUMENTS

| 5,441,955 | A | 8/1995 | Baker et al. |
| 5,830,615 | A | 11/1998 | Miyamoto et al. |
| 6,284,772 | B1 | 9/2001 | Pitzer et al. |
| 6,531,487 | B2 | 3/2003 | Pitzer et al. |
| 8,034,953 | B2 | 10/2011 | Combs |
| 8,193,185 | B2 | 6/2012 | Valiante |
| 9,617,272 | B2 | 4/2017 | Kumar et al. |
| 9,630,969 | B2 | 4/2017 | Li et al. |

FOREIGN PATENT DOCUMENTS

| CA | 2369448 A1 | 10/2000 |
| CN | 102579452 A | 7/2012 |
| CN | 103054870 A | 4/2013 |
| CN | 103570726 B | 7/2013 |
| CN | 103570727 A | 2/2014 |
| CN | 102532144 B | 9/2014 |
| EP | 1594524 B1 | 8/2012 |
| WO | WO 1995/013807 A1 | 5/1995 |
| WO | WO 2000/018769 A2 | 4/2000 |
| WO | WO 2000/061159 A1 | 10/2000 |
| WO | WO 2004/064759 A2 | 8/2004 |
| WO | WO 2006/122150 A1 | 11/2006 |
| WO | WO 2013/107164 A1 | 7/2012 |
| WO | WO2013/107164 A1 * | 7/2013 | ........... C07D 487/04 |
| WO | WO 2014/159248 A1 | 10/2014 |
| WO | WO 2015/006520 A1 | 1/2015 |
| WO | WO 2015/007249 A1 | 1/2015 |
| WO | WO 2015/070766 A1 | 5/2015 |
| WO | WO 2015/082499 A2 | 6/2015 |
| WO | WO 2015/091862 A1 | 6/2015 |
| WO | WO 2015/121812 A1 | 8/2015 |

OTHER PUBLICATIONS

Adams, et al. (2015) Nature Reviews: Drug Discover 14:603-621 (Published Online Jul. 31, 2015) entitled: "Big opportunities for small molecules in immuno-oncology".  
Baban, et al. (2011) J. Immunol 187:2329-2335 (pre-published online Aug. 3, 2011) entitled "Physiologic Control of IDO Competence in Splenic Dendritic Cells".  
Chen, et al. (2008) J Immunol. 181(8): 5396-5404; entitled; The indoleamine 2,3-dioxygenase pathway is essential for human plasmacytoid dendritic cell-induced adaptive T regulatory cell generation.  
Curti, et al. (2009) Blood 113(11): 2394-2401; entitled "The role of indoleamine2,3-dioxygenase in the induction of immune tolerance: focus on hematology".  
Dolusic and Frederick (2013) Expert Opin. Ther. Patents (2013) 23(10):1-15 entitled "Indoleamine 2,3-dioxygenase inhibitors: a patent review (2008-2012)".

(Continued)

*Primary Examiner* — Rebecca L Anderson  
(74) *Attorney, Agent, or Firm* — Sheppard Mullin Richter & Hampton LLP

(57) ABSTRACT

The present invention relates to an N-benzyl tryptanthrin derivative, and preparation method and use thereof. The N-benzyl tryptanthrin derivative of the present invention is characterized in that the derivative has a structural general formula as represented by formula 1, wherein each group is defined as in the specification. The preparation method of the compound is simple, has mild conditions and high yield, and is suitable for industrial production. The N-benzyl tryptanthrin derivative has good indoleamine-2,3-dioxygenase (IDO) inhibitory activity, and can be used for treating diseases having the pathological feature of IDO-mediated tryptophan metabolism.

(1)

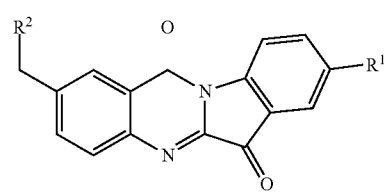

15 Claims, No Drawings

(56) References Cited

OTHER PUBLICATIONS

Friberg, et al (2002) Int. J. Cancer 101:151-155; entitled "Indoleamine2,3-dioxygenase Contributes to Tumor Cell Evasion of T-Cell Mediated Rejection".

Hoomgaard, et al. (Jun. 2013) J. Exp. Med.; entitled "Indoleamine 2,3-dioxygenase is a critical resistance mechanism in antitumor T cell immunotherapy targeting CTLA-4".

Huang, et al. (2011) Eur. J. of Medicinal Chemistry 46:5680-5687; entitled "Structure-activity relationship and enzyme kinetic studies in 4-aryl-1H-1,2,3-triazoles and indoleamine 2,3,-dioxygenase (IDO) inhibitors".

Kong, et al (2009) Chinese Journal of Medicinal Chemistry 19(2):147-154; entitled "Recent advance of IDO inhibitors" (Original in Chinese; no translation provided).

Quershi, et al (2013) Science Vision 19:33-40; entitled "Indoleamine 2,3,-dioxygenase: Potential in Cancer Immunotherapy".

Platten, et al (2012) Cancer Research 71(21):OF1-OF6; entitled "Tryptophan Catabolism in Cancer: Beyond IDO and Tryptophan Depletion".

Smith, C. and Prendergast, G. (Jun. 2013) Atlas Genet. Cytogenet. Oncol. Haematol. 17(12):856-862; entitled "Inflammatory programming and immune modulation in cancer by IDO".

Koblish, et al (2010) Mol Cancer Ther; 9(2):489-498; entitled "Hydroxamidine Inhibhitors of Indoleamine 2,3,-dioxygenase Potently Suppress System Tryptophan Catabolism and the Growht of IDO-Expressing Tumors".

Huang, et al (Jun. 2013) Bioanalysis 5(11):1-11; entitled "A simple LC-MS/MS method for determination of kynurenine and tryptophan concentrations in human plasma from HIV infected patients".

Littlejohn, et al (2000) Protein Expression and Purification 19:22-29; entitled "Expression and Purification of Recombinant Human Indoleamine 2,3,-Dioxygenase".

Liu, et al (2000) Blood 115(7):3520-3530; entitled "Selective inhibition of IDO1 effectively regulates mediators of antitumor immunity".

Manches, et al (2008) J. Clin. Investigation 118(10):3431-3439; entitled "HIV-activated human plasmacytoid DCs induce Tregs through an indoleamine 2,3-dioxygenase-dependent mechanism".

Metz, et al (2012) Oncoimmunology 1:1460-1468; entitled "IDO inhibits a tryptophan sufficiency signal that stimulates mTOR a novel IDO effector pathway targeted by D-1-methyl-tryptophan".

Muller, et al (2005) Nature Medicine 11(3):312-319 entitled "Inhibition of indoleamine 2,3-dioxygenase, an immunoregulatory target of the cancer suppression gene Bin1, potentiates cancer chemotherapy".

Munn, D. (2012) Frontiers in Bioscience E4,734-745; entitled "Blocking IDO activity to enhance anti-tumor immunity".

Munn, D and Mellor, A (2007) J. Clin. Invest 117(5):1147-1154; entitled "Indoleamine 2,3-dioxygenase and tumor-induced tolerance".

Munn, D. and. Mellor, A (Mar. 2013) Trends Immunol. 34(3):137-143; entitled "Indoleamine 2,3 dioxygenase and metabolic control of immune responses".

Reddy, et al (2008) J. Clin. Invest. 118:2562-2573; entitled "Histone deacetylase inhibition modulates indoleamine 2,3-dioxygenase—dependent DC functions and regulates experimental graft-versus-host disease in mice".

Robrig, et al (2012) | J. Med. Chem. 55, 5270-5290; entitled "Rational Design of 4-Aryl-1,2,3-Triazoles for Indoleamine 2,3Dioxygenase 1 Inhibition".

Rustin, G. (2011) Annals of Oncology 22(supplement 8): viii45-viii48; entitled "Follow-up with CA125 after primary therapy of advanced ovarian cancer has major implications for treatment outcome and trial performances and should not be routinely performed".

Sharma, et al (2007) J. Clin. Invest. 117:2570-2582; entitled "Plasmacytoid dendritic cells from mouse tumor-draining lymph nodes directly activate mature Tregs via indoleamine 2,3-dioxygenase".

Spranger, et al. (Aug. 2014) Science Translational Medicine 5:1-21; Author Manuscript entitled "Up-Regulation of PD-L1, IDO, and Tregs in the Melanoma Tumor Microenvironment Is Driven by CD8+ T Cells" Published in Final Form at Science Translational Medicine Aug. 28, 2013; 5(200).

Yang, et al. (Oct. 2013) J. Med. Chem 56:8321-8331; entitled "Discovery of Tryptanthrin Derivatives as Potent Inhibitors of Indoleamine 2,3-Dioxygenase with Therapeutic Activity in Lewis Lung Cancer (LLC) Tumor-Bearing Mice" and supporting information entitled "Supporting Information for: Discovery of Tryptanthrin Derivatives as Potent Inhibitors of Indoleamine 2, 3-Dioxygenase with Therapeutic Activity in LLC tumor-bearing Mice".

Yu, et al (2010) J. of Alzheimers Disease 22:257-266; entitled "Oren-gedoku-to and its Constituents with Therapeutic Potential in Alzheimer's Disease Inhibit Indoleamine 2, 3-Dioxygenase Activity In Vitro".

Yue, et al (2009) J. Med. Chem. 52:7364-7367; entitled "Discovery of Potent Competitive Inhibitors of Indoleamine 2,3-Dioxygenase with in Vivo Pharmacodynamic Activity and Efficacy in a Mouse Melanoma Model" and supporting information entitled: Supporting Information: Yue, et al; Discovery of Potent Competitive Inhibitors of Indoleamine 2,3 Dioxygenase with In Vivo Pharmacodynamic Activity and Efficacy in a Mouse Melanoma Model.

Swanson, et al. (2004) Am. J. Respir. Cell Mol. Biol 30:311-318; entitled "CDllc+ Cells Modulate Pulmonary Immune Responses by Production of Indoleamine 2,3-Dioxygenase".

Rose, D.P. (1972) J. Clinical Pathology 25:17-25; entitled "Aspects of tryptophan metabolism in health and disease: a review."

Blankfield, A. (2012) International Journal of Tryptophan Research 5:27-32; entitled "A Brief Historic Overview of clinical Disorders Associated with Tryptophan: The Relevance to chronic Fatigue syndrome (cFs) and Fibromyalgia (FM)".

Fowkes, et al. (1992) ForeFront—Health Investigations; entitled "Tryptophan Metabolism in Chronic Disease and Aids".

Takikawa et al. (1998) J. Biol. Chem. 263(4):2041-2048; entitled "Mechanism of Interferon-$\gamma$ Action".

Lin et al. (2016) J. Med. Chem. 59(1):419-430; entitled "Phenyl benzenesulfonylhydrazides exhibit selective indoleamine 2,3-dioxygenase inhibition with potent in vivo pharmacodynamic activity and antitumor efficacy" (including supporting information).

International Search Report for International Application No. PCT/CN2014/090947, dated Feb. 17, 2015.

Extended European Search Report for EP Application No. 14861381.3, dated Mar. 29, 2017.

Search Report for Chinese Application No. 2013105605720, dated Jun. 3, 2015.

Tojo et al., "Crystal structures and structure-activity relationships of imidazothiazole derivatives as IDO1 inhibitors," ACS Med. Chem. Lett, 5(10):1119-1123 (2014).

Prendergast et al., "ndoleamine 2,3-dioxygenase pathways of pathogenic inflammation and immune escape in cancer," Cancer Immunol. Immunother., 63(7):721-735 (2014).

Written Opinion for Singapore Application No. 11201603716Y, dated Jun. 13, 2017.

Written Opinion for Singapore Application No. 11201603716Y, dated Apr. 19, 2018.

* cited by examiner

N-BENZYL TRYPTANTHRIN DERIVATIVE, AND PREPARATION METHOD AND APPLICATION THEREOF

TECHNICAL FIELD

The present invention belongs to the technical field of pharmaceutical chemistry and specifically relates to an N-benzyl tryptanthrin derivative, and preparation method and application thereof.

PRIOR ART

Indole-2,3-dioxygenase (abbreviated as IDO; MW 48,000; EC 1.13.11.42) is a heme-containing enzyme which constitutes the first enzyme, as well as a rate-limiting enzyme in the mammalian tryptophan metabolism pathway. IDO catalyzes an oxidation reaction in which the essential amino acid tryptophan undergoes double oxidation to produce N-formylkynurenine and is responsible for the physiological clean-up of tryptophan in vivo. By degrading tryptophan, IDO produces a tryptophan-poor microenvironment in vivo, thereby resulting in the occurrence of various diseases which are closely linked to the lack of tryptophan, such as cancer, cataracts and neurological disorders. Therefore, the search for a highly efficient inhibitor which targets IDO has become a focus of drug research and development in recent years.

IFN-γ is one of a number of potential inducers of IDO expression. During continued activation under a high level of IFN-γ stimulation, IDO reduces the availability of free serum tryptophan, thus reducing 5-hydroxytryptamine production. These changes, in conjunction with the accumulation of neurologically active kynurenine metabolites, such as quinolinic acid (also induced by IDO), promote the onset of neurological/psychiatric disorders and act as the cause of a variety of psychological disorders, while also inducing symptoms associated with chronic diseases characterized by IDO activity and tryptophan degradation.

IDO activity also relates to the onset of age-related nuclear cataracts. IDO is the first enzyme involved in UV filter biosynthesis in the lens and is also the rate-limiting enzyme. Modifications to UV filter compounds derived from the degradation of tryptophan (3-hydroxykynurenine and kynurenine glucoside) are present in human lens proteins. The amount of these UV filter compounds increases with age, gradually causing the lens to become cloudy, which further leads to so-called age-related nuclear cataracts.

IDO expression also relates to the suppression of an immune response caused by blocking local T-lymphocyte proliferation. T-lymphocytes are very sensitive to a lack of tryptophan and T-lymphocytes will be arrested in the G1 phase of the cell cycle in the absence of tryptophan. This T cell-mediated immune response suppression is the cause of many diseases, including autoimmune diseases, allograft rejection, neurodegenerative disorders, depression, bacterial or viral infections (e.g. the human immunodeficiency virus (HIV)) and cancer (Swanson et al. Am. J. Respir. Cell Mol. Biol. 2003, 30, 311).

It has been found that most human tumors constitutively express IDO. Murine tumor cells obtained from previously immunized mice have shown that expression of IDO can provide protection from rejection, and administration of 1-MT eliminates the aforementioned effect. Furthermore, concomitant administration of an IDO inhibitor improved the effectiveness of cancer treatment.

IDO inhibitors may be used in the control of mental disorders, as well as the treatment of other diseases which include the IDO-mediated metabolism of tryptophan as a pathological feature; said diseases including viral infections such as AIDS, bacterial infection such as Lyme disease and streptococcal infection, neurodegenerative disorders (e.g., Alzheimer's disease, Huntington's disease and Parkinson's disease), depression, cancer (including T-cell leukemia and colon cancer), ocular diseases (such as cataracts and age-related yellowing) and autoimmune diseases. A variety of different in vitro assays (Takikawa, et al. J. Biol. Chem. 1998, 263, 2041) can be used to filter (for example, via high throughput screening) and measure the IDO inhibition activity of a reaction reference or extracts obtained from natural sources, or determine IDO inhibition-related kinetic constants.

IDO is closely linked to the pathogenesis of many different diseases and has already been shown to be a target for cancer, Alzheimer's disease, depression, cataracts and other serious diseases. IDO inhibitors have broad prospects for application as drugs, but so far no suitable IDO inhibitor has been marketed as a drug; therefore, the search for a novel, efficient IDO inhibitor has important theoretical significance and potential applied value.

Existing studies have shown that the IDO inhibitor 1-MT (1-methyl-tryptophan) can enhance the sensitivity of tumor cells to T-cell immune stimulation in vitro; and the same agent is capable of retarding the growth of tumor cells and enhancing chemotherapy drug anti-tumor efficacy in vivo in animal models, with effects observed for virtually all spontaneously occurring tumors. Unfortunately, the inhibition efficiency of most existing IDO inhibitors is low, and the inhibition constant (Ki) of the most commonly used IDO inhibitor in in vivo and in vitro trials, 1-MT, is a mere 34 μM. Thus, there is an urgent need in this field to develop a novel, efficient IDO inhibitor.

DESCRIPTION OF THE INVENTION

The objective of the present invention is the provision of an N-benzyl tryptanthrin derivative, and preparation method and application thereof.

The first aspect of the present invention provides an N-benzyl tryptanthrin derivative, wherein said derivative has the general structure as shown in Formula 1 below.

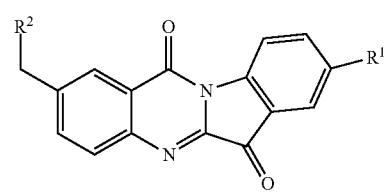

where
$R^1$ corresponds to hydrogen or fluorine;
$R^2$ corresponds to —$NR^3R^4$;
$R^3$ and $R^4$ are each independently selected from the following set: H, substituted or unsubstituted C1-C4 alkyl groups, substituted or unsubstituted C2-C4 alkenyl groups, substituted or unsubstituted C2-C4 alkynyl groups, and substituted or unsubstituted C3-C6 cycloalkyl groups;
or $R^3$ and $R^4$ forms a substituted or unsubstituted 5-7 membered heterocyclic ring with an adjacent nitrogen atom, where said 5-6 membered saturated ring includes 1-2 nitrogen atoms as well as 0-2 heteroatoms selected from the following set: O and S;
here, substitution refers to cases in which one or more hydrogen atoms present on a given group (preferably hydrogen atoms present on a nitrogen atom) are substituted by a substituent selected from the following set: C1-C4 alkyl groups, C1-C4 haloalkyl groups, amino-protecting groups (preferably t-butoxycarbonyl) and halogens.

In another preferred embodiment, when $R^3$ and $R^4$ together with an adjacent nitrogen atom form a substituted or unsubstituted 5-6 membered saturated ring, the nitrogen atom present on the ring may optionally bear an amino-protecting group.

In another preferred embodiment, said amino-protecting group is selected from the following set:

In another preferred embodiment, said 5-7 membered heterocyclic ring is not a heteroaryl ring.

In another preferred embodiment, said 5-7 membered heterocyclic ring is a saturated heterocyclic ring, preferably a 5-6 membered saturated heterocyclic ring.

In another preferred embodiment, said 5-7 membered heterocyclic ring contains only one or two heteroatoms.

In another preferred embodiment, all of the heteroatoms of said 5-7 membered heterocyclic ring are constituted by N.

In another preferred embodiment, $R^3$ and $R^4$ together are each independently selected from the following set: C1-C4 alkyl groups; or, $R^3$ and $R^4$ together with an adjacent nitrogen atom form a substituted or unsubstituted 5-6 membered saturated ring, where said 5-6 membered saturated ring includes 1-2 nitrogen atoms, as well as an optional one heteroatom selected from the following set: O.

In another preferred embodiment, $R^3$ and $R^4$ are not simultaneously constituted by H.

In another preferred embodiment, $R^2$ is a cyclic imine.

In another preferred embodiment, $R^2$ is a substituted or unsubstituted group selected from the following set:

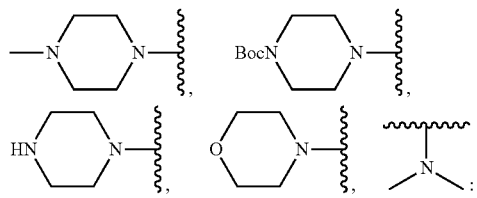

where ⌇ indicates a connection site;
here, substitution refers to cases in which one or more hydrogen atoms present on a given group are substituted by a substituent selected from the following set: C1-C4 alkyl groups and halogens.

In another preferred embodiment, $R^1$ corresponds to F.

The second aspect of the present invention provides an N-benzyl tryptanthrin derivative, wherein the general structure of said derivative is as shown below:

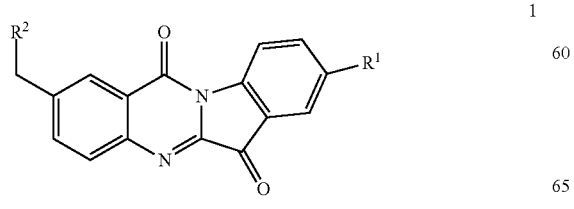

1

$R^1$=H or F

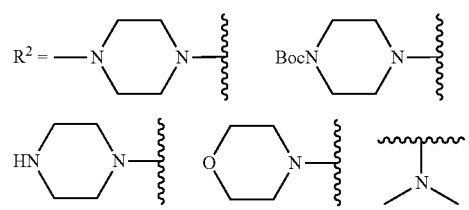

where the substituent $R^2$ corresponds to a cyclic imine or dialkyl-substituted amine and $R^1$ corresponds to hydrogen or fluorine.

In another preferred embodiment, said derivative is a compound selected from the following set:

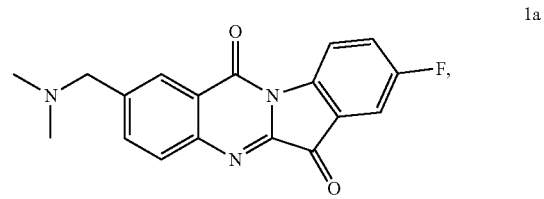

1a

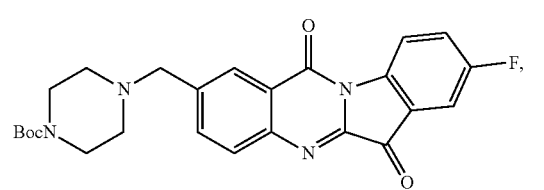

1b

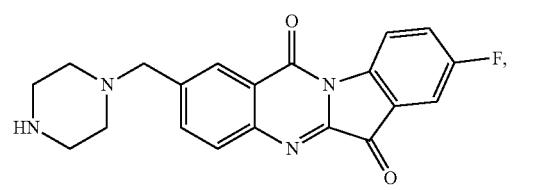

1c

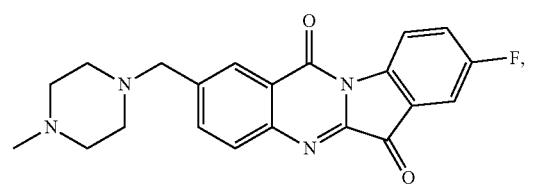

1d

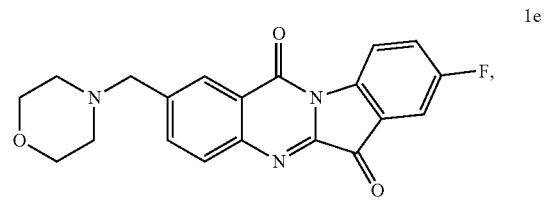

1e

-continued

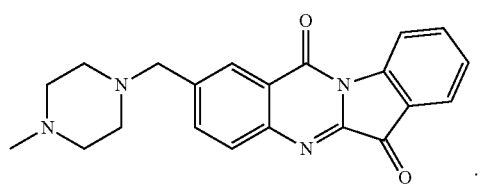

1f

The third aspect of the present invention provides a method for the preparation of an N-benzyl tryptanthrin derivative as given in the first or second aspects of the present invention, where said method includes the following steps:

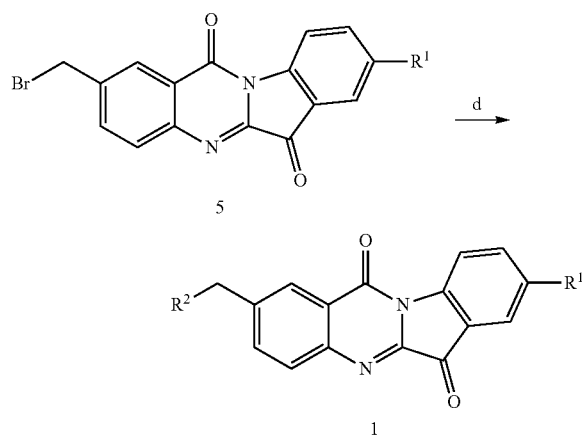

(d) The compound given in Formula 5 (2-bromomethyl-tryptanthrin) is reacted with $R^2H$ in an inert solvent in the presence of triethylamine to obtain the compound shown in Formula 1;

where $R^1$ and $R^2$ are as defined above.

In another preferred embodiment, in Step (d), said inert solvent is constituted by DMF, preferably anhydrous DMF.

In another preferred embodiment, in Step (d), said reaction is carried out at approximately 10-40° C.

In another preferred embodiment, in Step (d), the duration of said reaction is 0.5-12 hours, with a range of 1-5 hours being preferable.

In another preferred embodiment, in Step (d), the molar ratio of the compound given in Formula 5, $R^2H$ and triethylamine is 1:(1-2):(2-5).

In another preferred embodiment, said method further includes a Step (c) prior to Step (d):

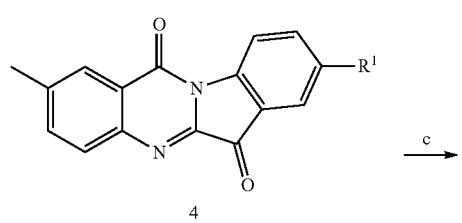

-continued

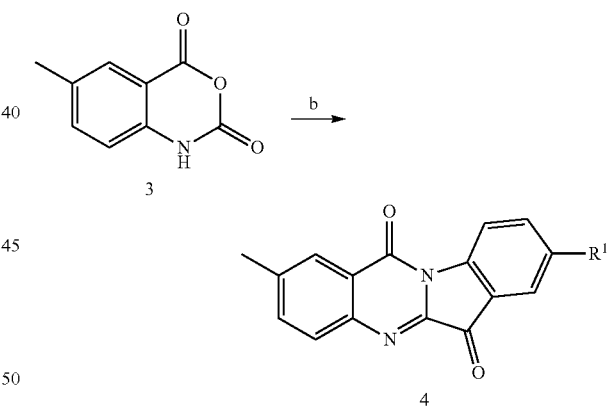

(c) The compound given in Formula 4 is reacted with a bromination agent in an inert solvent to obtain the compound given in Formula 5; where the bromination agent used is preferably NBS.

In another preferred embodiment, the reaction in Step (c) is carried out in the presence of an initiator, and preferably carried out in the presence of AIBN.

In another preferred embodiment, Step (c) includes: mixing NBS and AIBN, followed by reacting with the compound given in Formula 4.

In another preferred embodiment, the inert solvent indicated in Step (c) is dichloromethane, with anhydrous dichloromethane being preferable.

In another preferred embodiment, in Step (c), said reaction is carried out at approximately 75-85° C.

In another preferred embodiment, in Step (c), the duration of said reaction is 15-17 hours.

In another preferred embodiment, in Step (c), the molar ratio of the compound given in Formula 4, NBS and AIBN is 1:1:(0.005-0.02).

In another preferred embodiment, said method further includes a Step (b) prior to Step (c):

(b) The compound given in Formula 3 is reacted with in an inert solvent in the presence of triethylamine to obtain the compound shown in Formula 4.

In another preferred embodiment, in Step (b), said inert solvent is constituted by toluene, preferably anhydrous toluene.

In another preferred embodiment, in Step (b), said reaction is carried out at approximately 100-120° C.

In another preferred embodiment, in Step (b), the duration of said reaction is 3.5-4.5 hours.

In another preferred embodiment, in Step (b), the molar ratio of the compound given in Formula 3,

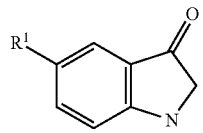

and triethylamine is (0.2-0.5):(0.2-0.5):1.

In another preferred embodiment, said method further includes a Step (a) prior to Step (b):

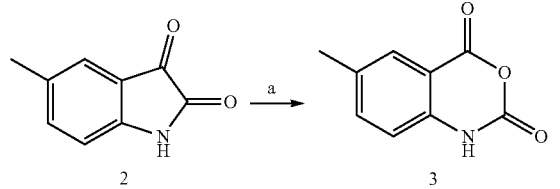

(a) The compound given in Formula 2 is reacted with an oxidizing agent in an inert solvent to obtain the compound given in Formula 3; where the oxidizing agent used is preferably meta-chloroperoxybenzoic acid.

In another preferred embodiment, the inert solvent indicated in Step (a) is dichloromethane, with anhydrous dichloromethane being preferable.

In another preferred embodiment, in Step (a), said reaction is carried out at room temperature (with a range of 10-40° C. being preferable).

In another preferred embodiment, in Step (a), the duration of said reaction is 1.5-2.5 hours.

In another preferred embodiment, in Step (a), the molar ratio of the compound given in Formula 2 and the oxidizing agent (0.5-1):1.

The fourth aspect of the present invention provides a method for the preparation of an N-benzyl tryptanthrin derivative as given in the second aspect of the present invention, where the synthesis route is as described below:

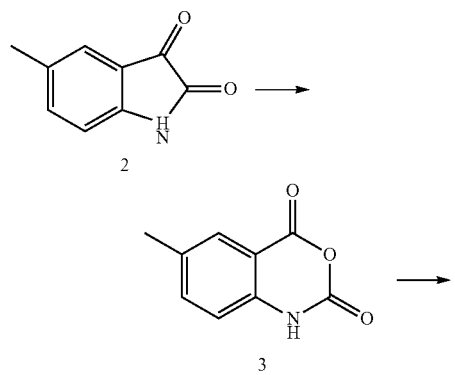

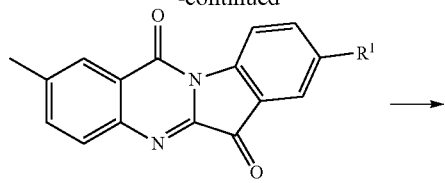

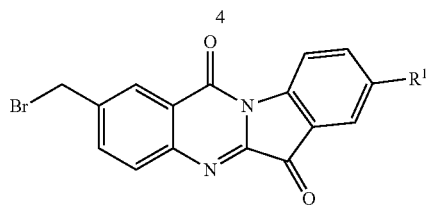

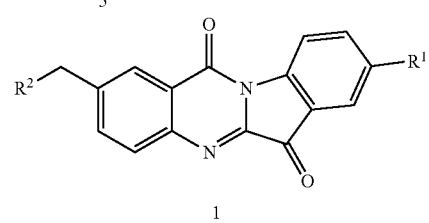

$R^1$=H or F

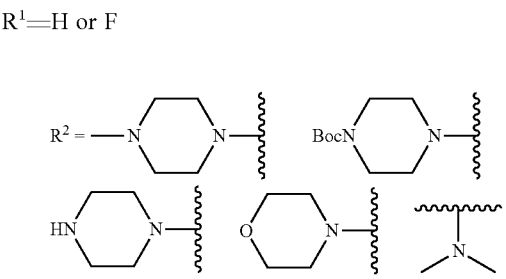

The specific steps are as follows:

(1) Synthesis of Methylisatoic Anhydride (3)

Suspend 5-methylisatin in dry dichloromethane and add meta-chloroperoxybenzoic acid batchwise at 0° C., then stir for 1.5-2.5 hours at room temperature; once the reaction is confirmed as being complete via TLC, filtering off the white solid produced in the reaction and washing thrice with ethyl acetate to obtain 5-methylisatoic anhydride; note that the molar ratio of 5-methylisatin and meta-chloroperoxybenzoic acid is (0.5-1):1;

(2) Synthesis of 2-Methyltryptanthrin (4)

Suspend a mixture of methylisatoic anhydride, 5-fluoroisatin and triethylamine in dry toluene, then heat for 3.5-4.5 hours at a temperature of 100-120° C. and distill off the solvent under reduced pressure; dissolve the resulting yellow solid in dichloromethane and add ethyl acetate, then filter the resulting yellow solid and wash with ethyl acetate three times to obtain 2-methyltryptanthrin; note that the molar ratio of methylisatoic anhydride, 5-fluoroisatin and triethylamine is (0.2-0.5):(0.2-0.5):1;

(3) Synthesis of 2-bromomethyl-tryptanthrin (5)

Dissolve the 2-methyltryptanthrin obtained in Step (2) in dry dichloromethane at 75-85° C. under the protection of nitrogen gas, then add in a mixture of NBS and AIBN batchwise. Heat the reaction solution to 75° C. for 15-17 hours and confirm that the reaction is completed via TLC. Once the reaction solution cools to room temperature, performing washing with a salt solution and drying over anhydrous sodium sulfate to obtain a concentrated yellow product; note that the molar ratio of 2-methyltryptanthrin, NBS and AIBN is 1:1:(0.005-0.02);

(4) Synthesis of N-Benzyltryptanthrin (1)

Stir together 2-bromomethyl-tryptanthrin, an aliphatic amine and triethylamine at room temperature in dry DMF for 1.5-2.5 hours, and once the reaction is verified as being complete via TLC, adding 50 ml of water and performing three sequential extractions using 10 ml of dichloromethane; next, subject the entire volume of dichloromethane obtained to three washes with water and then dry over anhydrous sodium sulfate. Perform separation of the concentrated yellow solid obtained using silica gel to obtain a yellow colored N-benzyl tryptanthrin derivative; note that the molar ratio of 2-bromomethyl-tryptanthrin, the aliphatic amine and triethylamine is 1:(1-2):(2-5).

The fifth aspect of the present invention provides an application for the N-benzyl tryptanthrin derivative given in the first and second aspects of the present invention in the preparation of a drug designed to prevent and/or treat diseases which include a disorder of the IDO-mediated metabolism of tryptophan as a pathological feature.

The sixth aspect of the present invention provides an application for the compound given in Formula 1 as described in the first and second aspects of the present invention or a pharmaceutically acceptable salt thereof, to be used for:
(i) the preparation of an IDO inhibitor;
(ii) the preparation of a drug for the treatment of a tryptophan metabolism-related disease; and
(iii) non-therapeutic inhibition of IDO in vitro.

In another preferred embodiment, said tryptophan metabolism disorder-related disease is selected from the following set: tumors, depression, anxiety, AIDS, autoimmune diseases, mental disorders, Lyme disease infections, streptococcal infections, neurodegenerative disorders (such as Alzheimer's disease, Huntington's disease and Parkinson's disease), depression, cancer (including T-cell leukemia and colon cancer), ocular diseases (such as cataracts and age-related yellowing) and autoimmune diseases.

The seventh aspect of the present invention provides a pharmaceutical composition, where said pharmaceutical composition includes: (i) a compound given in Formula 1 as described in the first and second aspects of the present invention or pharmaceutically acceptable salts thereof; as well as (ii) a pharmaceutically acceptable carrier.

In another preferred embodiment, said pharmaceutical composition is used for the treatment of diseases associated with a disorder in the tryptophan metabolism.

In another preferred embodiment, said tryptophan metabolism disorder-related disease is selected from the following set: tumors, depression, anxiety, AIDS, autoimmune diseases, mental disorders, Lyme disease infections, streptococcal infections, neurodegenerative disorders (such as Alzheimer's disease, Huntington's disease and Parkinson's disease), depression, cancer (including T-cell leukemia and colon cancer), ocular diseases (such as cataracts and age-related yellowing) and autoimmune diseases.

The eighth aspect of the present invention provides an IDO inhibitor, where said IDO inhibitor includes a compound given in Formula 1 as described in the first and second aspects of the present invention, or a pharmaceutically acceptable salt thereof.

The ninth aspect of the present invention provides a method for non-therapeutically inhibiting IDO activity in vitro, where said method includes the following process: a compound given in Formula 1 as described in the first and second aspects of the present invention or a pharmaceutically acceptable salt thereof is brought into contact with an inhibition target in an amount which produces effective inhibition.

The tenth aspect of the present invention provides a method for the preparation of a pharmaceutical composition used to treat a disease associated with a disorder in the tryptophan metabolism, where, in said method: a compound given in Formula 1 as described in the first and second aspects of the present invention or a pharmaceutically acceptable salt thereof is mixed with a pharmaceutically acceptable carrier in a therapeutically effective amount to create a pharmaceutical composition.

The eleventh aspect of the present invention provides a method for treating a disease associated with a disorder in the tryptophan metabolism, where, in said method: a compound given in Formula 1 as described in the first and second aspects of the present invention or a pharmaceutically acceptable salt thereof is applied in a therapeutically effective amount to a treatment subject.

In another preferred embodiment, said tryptophan metabolism disorder-related disease is selected from the following set: tumors, depression, anxiety, AIDS, autoimmune diseases, mental disorders, Lyme disease infections, streptococcal infections, neurodegenerative disorders (such as Alzheimer's disease, Huntington's disease and Parkinson's disease), depression, cancer (including T-cell leukemia and colon cancer), ocular diseases (such as cataracts and age-related yellowing) and autoimmune diseases.

It should be noted that within the scope of the present invention, the aforementioned technical characteristics of the present invention and the technical characteristics described more specifically in the following text (e.g., the examples) can be combined with each other, thereby creating novel or preferred technical solutions. These are not listed exhaustively here due to space constraints.

DETAILED DESCRIPTION

Following long-term and in-depth research performed by the inventors of the present invention, the inventors unexpectedly discovered a type of N-benzyl tryptanthrin derivative with the structure as shown in Formula 1 which exhibits a highly specific IDO inhibitory activity, where the IDO inhibitory activity ($IC_{50}$) is unexpectedly significantly improved (the $IC_{50}$ value can fall by 1-3 orders of magnitude) in said compound versus certain other N-benzyl tryptanthrin derivatives having a highly similar structure, and said compound therefore has a good application potential. The present invention was completed by the inventors based on the aforementioned discovery.

Terms

Unless otherwise specified, all of the compounds pertaining to the present invention shall include all optical isomers or tautomeric forms thereof.

The term "C1-C4 alkyl group" refers to a straight or branched chain alkyl group having 1-4 carbon atoms such as methyl, ethyl, propyl, isopropyl, butyl, isobutyl, sec-butyl, tert-butyl or similar groups.

The term "C2-C4 alkenyl group" refers to a straight or branched alkenyl group having 2 to 4 carbon atoms such as ethenyl, propenyl, butenyl or similar groups.

The term "C2-C4 alkynyl group" refers to a straight or branched alkynyl group having 2 to 4 carbon atoms such as ethynyl, propynyl, butynyl or similar groups.

The term "5-7 membered heterocyclic ring" refers to a single ring containing 5-7 elements, where said ring does not have a completely conjugated n-electron system. In particular, in the context of the present invention, said ring may optionally contain 1-3 heteroatoms, where said heteroatoms include O and N. Representative examples of saturated rings include: a piperazinyl group, morpholino group, etc.

Unless otherwise specified, the term "substitution" refers to cases in which one or more hydrogen atoms present on a given group are substituted by a substituent selected from the following set: C1-C4 alkyl groups, C1-C4 haloalkyl groups, amino-protecting groups (preferably t-butoxycarbonyl) and halogens.

The term "halogen" refers to F, Cl, Br and I.

N-Benzyl Tryptanthrin Derivatives

Tryptanthrin is a type of indole quinazoline alkaloid, bearing the chemical name indolo[2,1-b]quinazoline-6,12-dione. Tryptanthrin is a yellow needle-like crystal in its pure form and can be found primarily in plants belonging to the indigo family, such as *Strobilanthes cusia, Polygonum tinctorium* and *Isatis tinctoria*. Alternatively, it can be extracted from a fermentation broth containing certain microorganisms.

Although tryptanthrin can be extracted from indigo plants as well as the metabolites of microorganisms, the separation process is long and yield is low, making it difficult to satisfy research-related and clinical drug demands. Only by exploring rapid, high yield, simple and readily available synthetic pathways can more resources be provided for tryptanthrin applications, making further research, development and application possible.

In order to overcome the deficiencies of existing techniques, the present invention has made structural modifications to tryptanthrin in order to improve the solubility and pharmacological activity of tryptanthrin, with the objective of obtaining an active compound with application value. Research and pharmacological testing pertaining to the present invention show that N-benzyl tryptanthrin derivatives which are produced by introducing a water soluble group into the tryptanthrin molecule have the potential to be more efficient as an IDO inhibitor, exhibiting various pharmacological activities, such as anti-bacterial, anti-inflammatory and anti-tumor activities, and having a wide application potential. Furthermore, compared to conventional methods for synthesizing tryptanthrin derivatives, the synthesis method constituted by the present invention offers the advantages of being simple to operate while using mild conditions and producing a high yield, making it more suitable for industrial production.

Specifically, the N-benzyl tryptanthrin derivative constituted by the present invention has the general structure as shown in Formula 1 below:

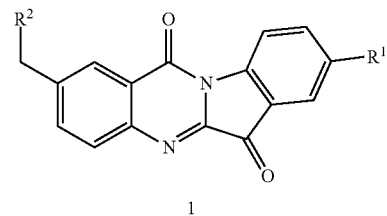

where
$R^1$ corresponds to hydrogen or fluorine;
$R^2$ corresponds to $-NR^3R^4$;
here, $R^3$ and $R^4$ are each independently selected from the following set: C1-C4 alkyl groups; or, $R^3$ and $R^4$ together with an adjacent nitrogen atom form a substituted or unsubstituted 5-6 membered saturated ring, where said 5-6 membered saturated ring includes at least one nitrogen atom as well as an optional 1-2 heteroatoms selected from the following set: O and N; here, substitution refers to cases in which one or more hydrogen atoms present on a given group (preferably hydrogen atoms present on a nitrogen atom) are substituted by a substituent selected from the following set: C1-C4 alkyl groups, t-butoxycarbonyl groups and halogens.

Preferably, $R^2$ should bear a nitrogen atom as well as a heteroatom selected from the following set: O and N.

Preferably, $R^2$ should be a substituted or unsubstituted group selected from the following set:

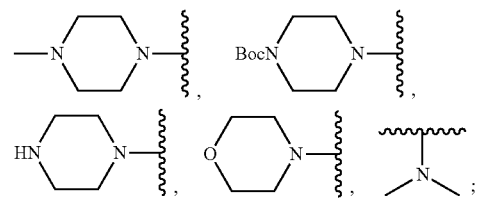

where "⸺" indicates a connection site;
here, substitution refers to cases in which one or more hydrogen atoms present on a given group are substituted by a substituent selected from the following set: C1-C4 alkyl groups and halogens.

The compound described by the present invention, the tautomeric forms, structural analogs or pharmaceutically acceptable salts thereof, as well as compositions containing at least one instance of said compound, a structural analog thereof or a pharmaceutically acceptable salt thereof can all be used to inhibit IDO, as well as in applications for the treatment and/or prevention of diseases which include the IDO-mediated tryptophan metabolism as a pathological feature. Such diseases include, but are not limited to, tumors, cancer, ocular diseases, autoimmune diseases, mental disorders, depression and anxiety. Said applications include in vitro and in vivo applications, as well as applications in the preparation of drugs, IDO inhibitors and pharmaceutical compositions. In particular, the inventors of the present invention discovered that, in a particularly preferred embodiment, when $R^1$ corresponds to F, the compound exhibits an optimal IDO inhibitory activity.

Preparation of N-Benzyl Tryptanthrin Derivatives

In recent years, pharmaceutical chemists have made extensive efforts to research the synthesis of tryptanthrin and its derivatives, and the main method used to synthesize tryptanthrin has been the reaction of isatin with isatoic anhydride; said method is simple, provides a high yield and uses mild reaction conditions. Furthermore, it is possible to add additional functional groups to the starting materials isatin and isatoic anhydride to synthesize a variety of different functional tryptanthrins. Currently, the main method used to synthesize isatin involves reacting chloral hydrate, hydroxylamine and aniline in aqueous hydrochloric acid to produce oximes, after which, ring closure is induced under concentrated sulfuric acid to obtain isatin; said method is extremely well suited to the synthesis of halogens and alkyl-containing tryptanthrins and provides a high yield. However, it is difficult to use this method to produce tryptanthrin containing active groups, due to the fact that said active groups readily produce byproduct reactions during the process of synthesizing isatin.

Following lengthy research efforts, the inventors of the present invention have successfully developed a synthesis method which can be used to prepare a tryptanthrin having active groups. In particular, said method includes the following step:

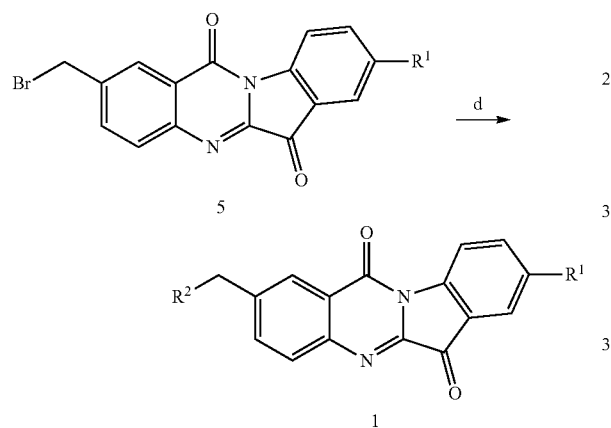

(d) The compound given in Formula 5 (2-bromomethyl-tryptanthrin) is reacted with $R^2H$ in an inert solvent in the presence of triethylamine to obtain the compound shown in Formula 1.

In another preferred embodiment, said method further includes the following step:

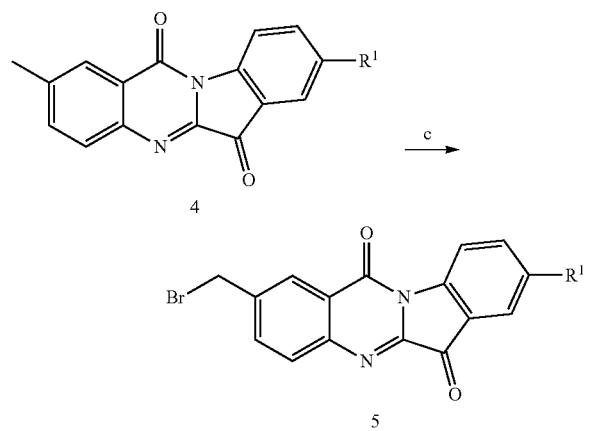

(c) The compound given in Formula 4 (2-methyltryptanthrin) is reacted with a bromination agent in an inert solvent to obtain the compound given in Formula 5; where the bromination agent used is preferably NBS.

In a preferred embodiment of the present invention, the bromination reaction is carried out in the presence of an initiator such as AIBN. A preferred embodiment includes: mixing NBS and AIBN, followed by a reacting with the compound given in Formula 4.

In another preferred embodiment, said method further includes the following step:

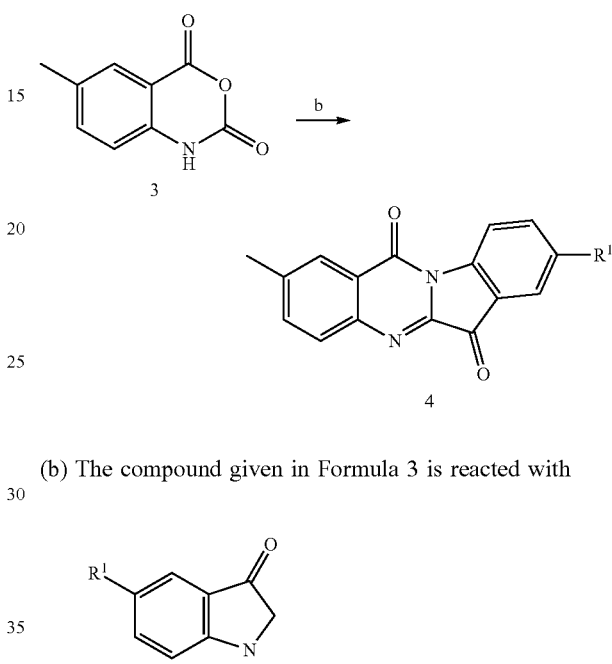

(b) The compound given in Formula 3 is reacted with

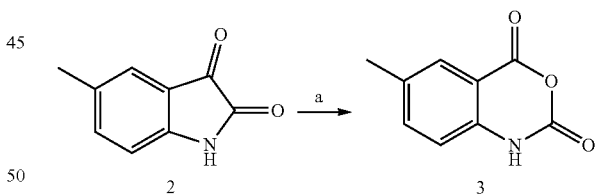

in an inert solvent in the presence of triethylamine to obtain the compound shown in Formula 4.

In another preferred embodiment, said method further includes the following step:

(a) The compound given in Formula 2 is reacted with an oxidizing agent in an inert solvent to obtain the compound given in Formula 3; where the oxidizing agent used is preferably meta-chloroperoxybenzoic acid.

The reaction times, reaction temperatures, etc., given in the aforementioned steps can be adjusted based on actual conditions; for example, methods common to the field (e.g., a TLC assay) can be used to confirm the end of the reaction. The solvents used in each step are not particularly restricted in any way, and inert solvents which do not react with the reactants which are common to the field can be used. It should be understood that once the aforementioned reaction scheme is disclosed in the present application, the specific conditions in each step can be established by a person skilled in the art given their existing knowledge within the field.

Among the methods for the preparation of N-benzyl tryptanthrin derivatives constituted by the present invention, an optimal synthesis route is given below:

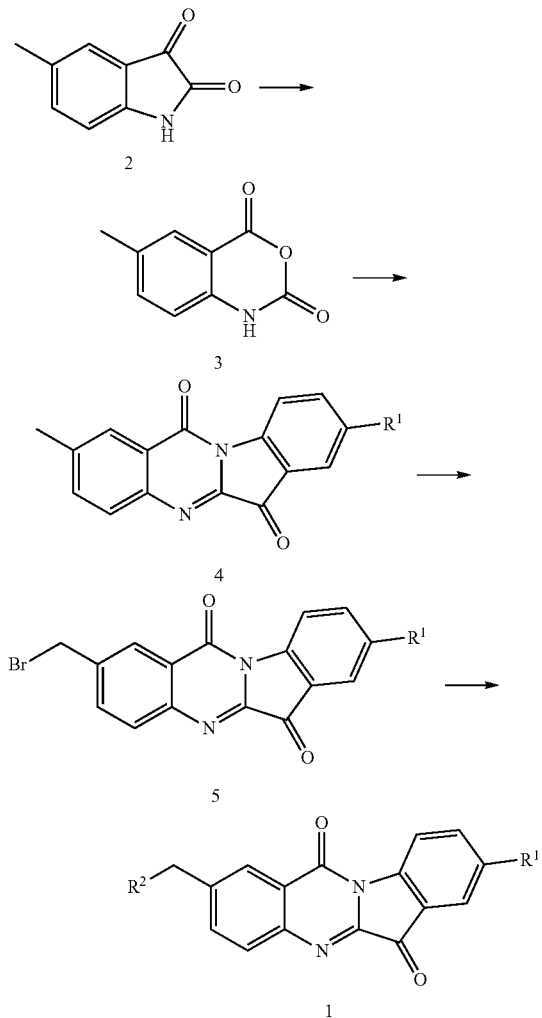

(1) Synthesis of Methylisatoic Anhydride (3)

Suspend 5-methylisatin in dry dichloromethane and add meta-chloroperoxybenzoic acid batchwise at 0° C., then stir for 1.5-2.5 hours at room temperature; once the reaction is confirmed as being complete via TLC, filtering off the white solid produced in the reaction and washing thrice with ethyl acetate to obtain 5-methylisatoic anhydride; note that the molar ratio of 5-methylisatin and meta-chloroperoxybenzoic acid is (0.5-1):1;

(2) Synthesis of 2-Methyltryptanthrin (4)

Suspend a mixture of methylisatoic anhydride, 5-fluoroisatin and triethylamine in dry toluene, then heat for 3.5-4.5 hours at a temperature of 100-120° C. and distill off the solvent under reduced pressure; dissolve the resulting yellow solid in dichloromethane and add ethyl acetate, then filter the resulting yellow solid and wash with ethyl acetate three times to obtain 2-methyltryptanthrin; note that the molar ratio of methylisatoic anhydride, 5-fluoroisatin and triethylamine is (0.2-0.5):(0.2-0.5):1;

(3) Synthesis of 2-bromomethyl-tryptanthrin (5)

Dissolve the 2-methyltryptanthrin obtained in Step (2) in dry dichloromethane at 75-85° C. under the protection of nitrogen gas, then add in a mixture of NBS and AIBN batchwise. Heat the reaction solution to 75° C. for 15-17 hours and confirm that the reaction is completed via TLC. Once the reaction solution cools to room temperature, performing washing with a salt solution and drying over anhydrous sodium sulfate to obtain a concentrated yellow product; note that the molar ratio of 2-methyltryptanthrin, NBS and AIBN is 1:1:(0.005-0.02);

(4) Synthesis of N-Benzyltryptanthrin (1)

Stir together 2-bromomethyl-tryptanthrin, an aliphatic amine and triethylamine at room temperature in dry DMF for 1.5-2.5 hours, and once the reaction is verified as being complete via TLC, adding 50 ml of water and performing three sequential extractions using 10 ml of dichloromethane; next, subject the entire volume of dichloromethane obtained to three washes with water and then dry over anhydrous sodium sulfate. Perform separation of the concentrated yellow solid obtained using silica gel to obtain a yellow colored N-benzyl tryptanthrin derivative. Here, the molar ratio of 2-bromomethyl-tryptanthrin, the aliphatic amine and triethylamine is 1:(1-2):(2-5).

In the above formulas, the definitions for each group are as given above.

IDO Inhibitors and their Applications

Due to the fact that the N-benzyl tryptanthrin derivative constituted by the present invention exhibits a highly specific IDO inhibitory activity, it can be used in the preparation of drugs used to treat and/or prevent diseases which include a disorder of the IDO-mediated metabolism of tryptophan as a pathological feature (such as tumors).

Said disease involving a disorder of the tryptophan metabolism includes any diseases which include a disorder of the IDO-mediated metabolism of tryptophan as a pathological feature which are known or unknown within the field, and preferably, said tryptophan metabolism disorder-related disease is selected from the following set: tumors, depression, anxiety, AIDS, autoimmune diseases, mental disorders, Lyme disease infections, streptococcal infections, neurodegenerative disorders (such as Alzheimer's disease, Huntington's disease and Parkinson's disease), depression, cancer (including T-cell leukemia and colon cancer), ocular diseases (such as cataracts and age-related yellowing) and autoimmune diseases.

Compared with Existing Techniques, the Present Invention Offers the Following Primary Advantages:

(1) The present invention provides a class of IDO inhibitors with a novel structure which, compared to compounds having similar structures, exhibit a surprising improvement in activity. Said compounds not only produce an IDO inhibitory activity, but they can also serve as further modified pharmaceutical intermediates at the same time, and have potential application value in the development of novel cancer treatment drugs.

(2) The present invention also provides a method for the synthesis of N-benzyl tryptanthrin derivatives, and said synthesis route offers the advantages of being simple to operate, employing mild reaction conditions, reducing solvent use, reducing pollution, etc., and is suitable for mass production.

In the following section the present invention will be further described by way of specific embodiment examples. It should be understood that these examples are merely illustrative of the present invention and are not intended to limit the scope of the present invention. For experimental methods included in the following embodiment examples which do not specify specific conditions, conventional conditions or conditions recommended by the manufacturer are used. Unless otherwise indicated, percentages and partial quantities are calculated by weight. Unless otherwise specified, the reagents and starting materials given in the following embodiment examples correspond to commercially available products. A specific synthesis route is given below:

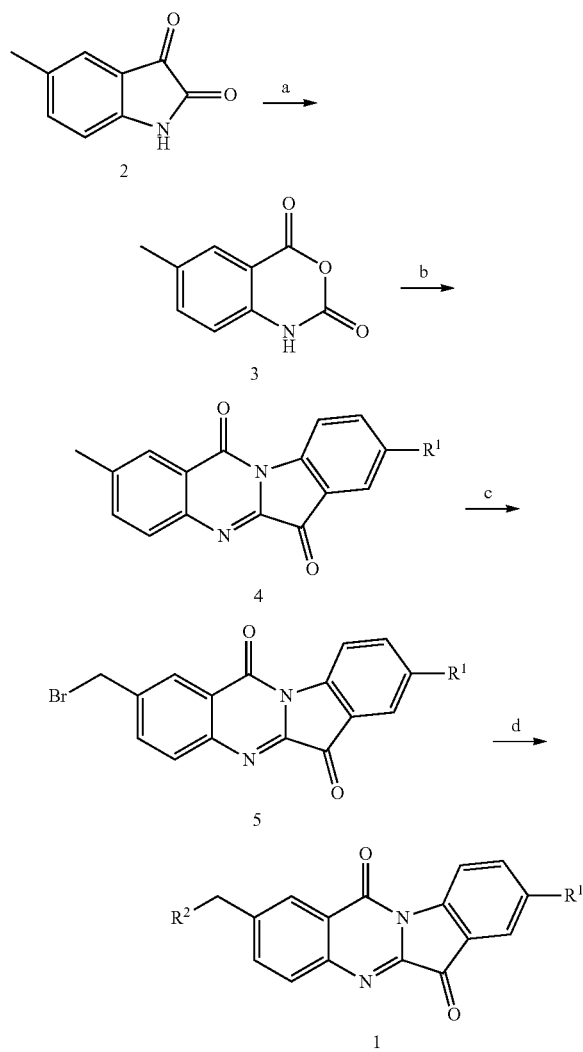

Reaction conditions for each step:
Step a. m-CPBA (2 eq.), CH$_2$Cl$_2$, RT;
Step b. Et$_3$N, toluene, reflux, 75%;
Step c. NBS, AIBN, CH$_2$Cl$_2$, reflux;
Step d. K$_2$CO$_3$, KI, DMF, amine.

Embodiment Example 1—Synthesis of 2-((dimethylamino) methyl)-8-fluoro-indolo[2,1-b]quinazoline-6,12-dione (1a)

The specific steps are as follows:

Step (1): Synthesis of 6-methyl-1H-benzo[d][1,3]oxazine-1,4-dione (3a)

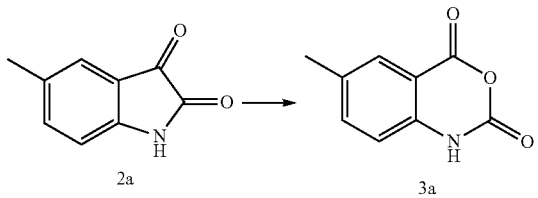

Compound 2a (500 mg, 3 mmol) was suspended in 10 ml of dry dichloromethane, after which meta-chloroperoxybenzoic acid (1.3 g, 6 mmol, 75%) was added batchwise at 0° C. TLC indicated that the reaction was complete after stirring the mixture for 2 hours at room temperature, after which, the white solid produced in the reaction was filtered off and three washes were performed with 10 ml ethyl acetate to obtain Compound 3a (350 mg, 65%).

Step (2): Synthesis of 8-fluoro-2-methyl-indolo[2,1-b]quinazoline-6,12-dione (4a)

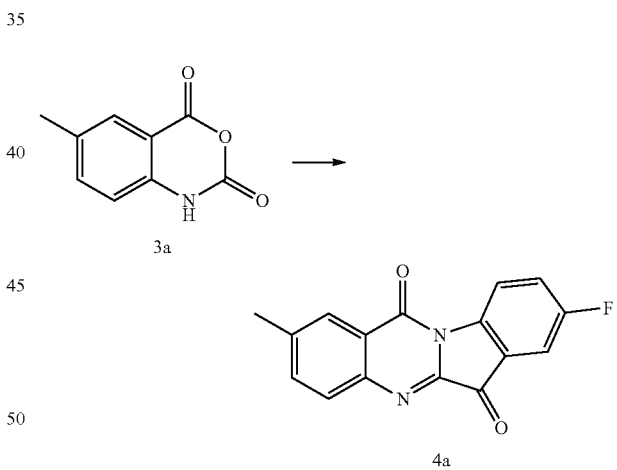

A mixture of Compound 3a (1 g, 5.6 mmol), 5-fluoroisatin (0.93 g, 5.6 mmol) and triethylamine (1.5 ml, 11.2 mmol) was suspended in dry toluene (10 ml) and heated at 110° C. for 4 hours. The solvent was distilled off under reduced pressure and the yellow solid thus obtained was dissolved in 2 ml of dichloromethane, after which 2 ml of ethyl acetate was added and the yellow solid was filtered and washed three times with 2 ml ethyl acetate to yield a yellow solid compound, i.e. Compound 4a (1.1 g, 75%).

Characterization Data:
$^1$H NMR (400 MHz, DMSO) δ 8.50 (dd, J=8.8, 4.2 Hz, 1H), 8.14 (s, 1H), 7.86 (d, J=8.2 Hz, 1H), 7.82-7.76 (m, 1H), 7.76-7.67 (m, 1H), 7.44-7.37 (m, 1H), 2.53 (s, 3H).

Step (3): Synthesis of 2-(bromomethyl)8-fluoro-indole[2,1-b]quinazoline-6,12-dione (5a)

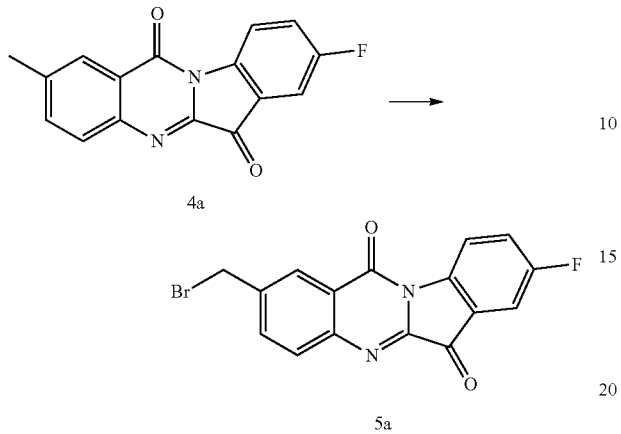

A mixture of NBS (381 mg, 2.14 mmol) and AIBN (29 mg, 0.18 mmol) was added in three batches to a dichloromethane solution (3.6 ml) containing Compound 4a (500 mg, 1.78 mmol) at a temperature of 80° C. under the protection of nitrogen gas. The reaction solution was heated to 80° C. for 16 hours. Once TLC confirmed that the reaction was complete, the reaction solution was cooled to room temperature, washed with a salt solution and dried over anhydrous sodium sulfate, to obtain a concentrated yellow product (5a).

Characterization Data:
$^1$H NMR (400 MHz, CDCl$_3$) δ 8.66 (dd, J=8.8, 4.0 Hz, 1H), 8.45 (d, J=1.9 Hz, 1H), 8.04 (d, J=8.3 Hz, 1H), 7.90 (dd, J=8.3, 2.1 Hz, 1H), 7.61 (dd, J=6.5, 2.6 Hz, 1H), 7.52 (td, J=8.6, 2.7 Hz, 1H), 4.65 (s, 2H).

Step (4): Synthesis of 2-((dimethylamino)methyl)-8-fluoroindolo[2,1-b]quinazoline-6,12-dione (1a)

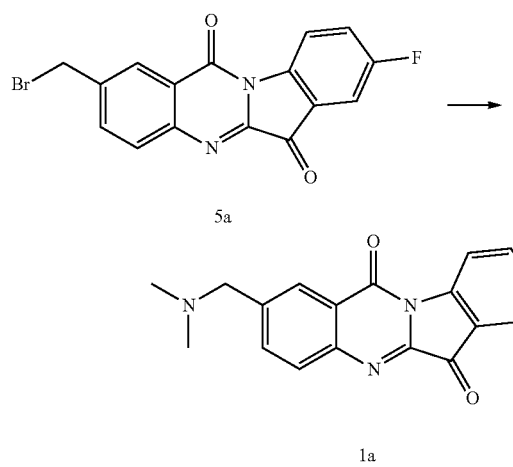

Compound 5a (500 mg, 1.39 mmol), dimethylamine hydrochloride (227 mg, 2.78 mmol), potassium iodide (10 mg) and triethylamine (0.5 ml) were stirred in a 5 ml solution of DMF at room temperature for 2 hours. Once TLC confirmed that the reaction was complete, 50 ml of water was added and three consecutive extractions were performed using 10 ml of ethyl acetate, after which the organic phase was washed three times with water and drying was performed over anhydrous sodium sulfate. The concentrated yellow solid obtained was subjected to separation using a silica gel column to obtain a yellow compound (1a).

Characterization Data:
$^1$HNMR (400 MHz, CDCl$_3$) δ 8.63 (dd, J=8.8, 4.1 Hz, 1H), 8.33 (d, J=1.5 Hz, 1H), 7.98 (d, J=8.3 Hz, 1H), 7.87 (dd, J=8.3, 1.8 Hz, 1H), 7.58 (dd, J=6.5, 2.6 Hz, 1H), 7.48 (td, J=8.7, 2.7 Hz, 1H), 3.61 (s, 2H), 2.30 (s, 6H).

Embodiment Example 2—Synthesis of 4-((8-fluoro-6,12-dioxo-6,12-dihydroxy-indolo[2,1-b]quinolin-2-yl)methyl)piperazine-1-carboxylic acid tert-butyl ester (1b)

Steps (1)-(3) are as specified in Embodiment Example 1.

Step (4): Synthesis of 4-((8-fluoro-6,12-dioxo-6,12-dihydroxy-indolo[2,1-b]quinolin-2-yl)methyl) piperazine-1-carboxylic acid tert-butyl ester (1b)

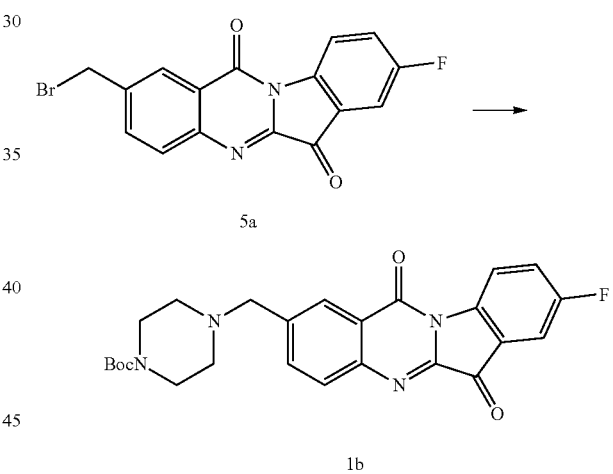

Compound 5a (500 mg, 1.39 mmol), N-Bocpiperazine (546 mg, 2.78 mmol), potassium iodide (10 mg) and triethylamine (0.5 ml) were stirred in a 5 ml solution of DMF at room temperature for 2 hours. Once TLC confirmed that the reaction was complete, 50 ml of water was added and three consecutive extractions were performed using 10 ml of ethyl acetate, after which the organic phase was washed three times with water and drying was performed over anhydrous sodium sulfate. The concentrated yellow solid obtained was subjected to separation using a silica gel column to obtain a yellow compound (1b).

Characterization Data:
$^1$H NMR (400 MHz, CDCl$_3$) δ 8.66 (dd, J=8.8, 4.0 Hz, 1H), 8.39 (d, J=1.5 Hz, 1H), 8.01 (d, J=8.3 Hz, 1H), 7.90 (dd, J=8.3, 1.8 Hz, 1H), 7.60 (dd, J=6.5, 2.6 Hz, 1H), 7.51 (td, J=8.6, 2.7 Hz, 1H), 3.71 (s, 2H), 3.47 (m, 4H), 2.46 (m, 4H), 1.48 (s, 9H).

Embodiment Example 3—Synthesis of 8-fluoro-2-(piperazin-1-ylmethyl)indolo[2,1-b]quinazoline-6,12-dione (1c)

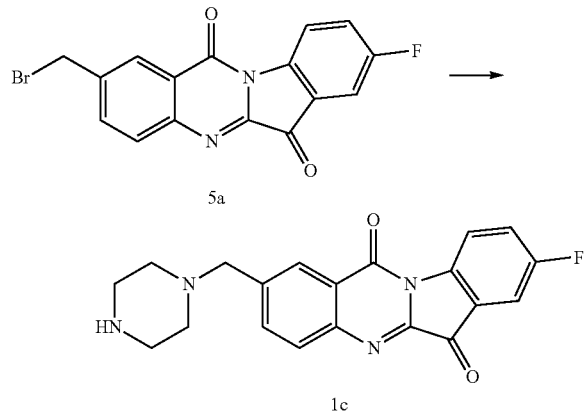

Steps (1)-(3) are as specified in Embodiment Example 1.

Step (4): Synthesis of 8-fluoro-2-(piperazin-1-ylmethyl)indolo[2,1-b]quinazoline-6,12-dione (1c)

Compound 5a (500 mg, 1.39 mmol), N-Bocpiperazine (546 mg, 2.78 mmol), potassium iodide (10 mg) and triethylamine (0.5 ml) were stirred in a 5 ml solution of DMF at room temperature for 2 hours. Once TLC confirmed that the reaction was complete, 50 ml of water was added and three consecutive extractions were performed using 10 ml of ethyl acetate, after which the organic phase was washed three times with water and drying was performed over anhydrous sodium sulfate to obtain a concentrated yellow solid. The yellow solid was dissolved in 3 ml of dichloromethane and a further ml of trifluoroacetic acid was added at room temperature. The reaction solution was stirred for one hour at room temperature, and once TLC ($CH_2Cl_2$/MeOH=10/1, Rf 0.2) confirmed that the reaction was complete, the solvent was removed under reduced pressure, 10 ml of a protective $NaHCO_3$ solution was added and ethyl acetate (10 ml×3) was used to perform extraction, after which, the organic phase was washed with a salt solution and drying was performed to obtain a concentrated solid which was subject to separation using a silica gel column to obtain a yellow solid compound (1c).
Characterization Data:
$^1$H NMR (400 MHz, $CDCl_3$) δ 8.65 (dd, J=8.8, 4.0 Hz, 1H), 8.37 (s, 1H), 8.00 (d, J=8.3 Hz, 1H), 7.89 (dd, J=8.3, 1.6 Hz, 1H), 7.59 (dd, J=6.5, 2.6 Hz, 1H), 7.50 (td, J=8.7, 2.7 Hz, 1H), 3.70 (s, 2H), 3.51-3.44 (m, 4H), 2.46 (s, 4H).

Embodiment Example 4—Synthesis of 8-fluoro-2-((4-methyl-piperazin-1-yl)methyl)indolo[2,1-b] quinazoline-6,12-dione (1d)

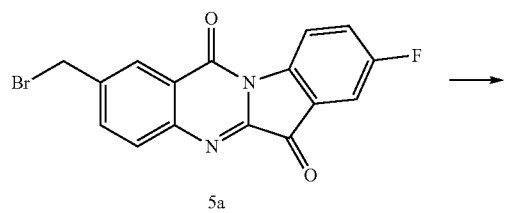

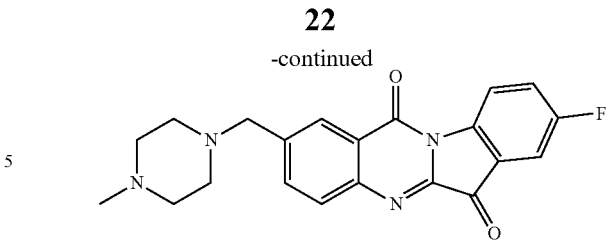

Steps (1)-(3) are as specified in Embodiment Example 1.

Step (4): Synthesis of 8-fluoro-2-((4-methyl-piperazin-1-yl) methyl)indolo[2,1-b]quinazoline-6,12-dione (1d)

Compound 5a (220 mg, 0.61 mmol), N-methylpiperazine (122 mg, 1.22 mmol), potassium iodide (10 mg) and triethylamine (0.5 ml) were stirred in a 5 ml solution of DMF at room temperature for 2 hours. Once TLC confirmed that the reaction was complete, 50 ml of water was added and three consecutive extractions were performed using 10 ml of ethyl acetate, after which the organic phase was washed three times with water and drying was performed over anhydrous sodium sulfate. The concentrated yellow solid obtained was subjected to separation using a silica gel column to obtain a yellow compound (1d).
Characterization Data:
$^1$H NMR (400 MHz, $CDCl_3$) δ 8.65 (dd, J=8.8, 4.0 Hz, 1H), 8.38 (d, J=1.5 Hz, 1H), 7.99 (d, J=8.3 Hz, 1H), 7.87 (dd, J=8.3, 1.8 Hz, 1H), 7.59 (dd, J=6.5, 2.6 Hz, 1H), 7.50 (td, J=8.7, 2.7 Hz, 1H), 3.50 (s, 2H), 2.59 (s, 8H), 2.38 (s, 3H).

Embodiment Example 5—Synthesis of 8-fluoro-2-((morpholino-1-yl)methyl)indolo[2,1-b]quinazoline-6,12-dione (1e)

Steps (1)-(3) are as specified in Embodiment Example 1.

Step (4): Synthesis of 8-fluoro-2-((morpholino-1-yl)methyl)indolo[2,1-b]quinazoline-6,12-dione (1e)

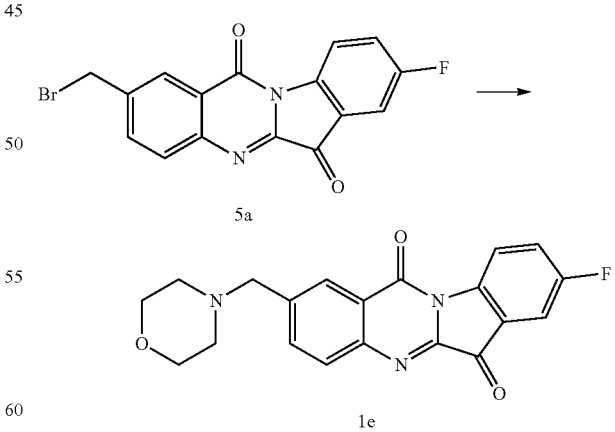

Compound 5a (500 mg, 1.39 mmol), morpholine (242 mg, 2.78 mmol), potassium iodide (10 mg) and triethylamine (0.5 ml) were stirred in a 5 ml solution of DMF at room temperature for 2 hours. Once TLC (EtOAc, Rf 0.5) confirmed that the reaction was complete, 50 ml of water was added and three consecutive extractions were performed using 10 ml of ethyl acetate, after which, the organic phase was washed three times with water and drying was performed over anhydrous sodium sulfate to obtain a concentrated yellow solid which was subjected to separation using a silica gel column (EtOAc) to obtain a yellow compound (1e).

Characterization Data:

$^1$H NMR (400 MHz, CDCl$_3$) δ 8.66 (dd, J=8.8, 4.1 Hz, 1H), 8.39 (s, 1H), 8.01 (d, J=8.3 Hz, 1H), 7.90 (dd, J=8.3, 1.7 Hz, 1H), 7.60 (dd, J=6.5, 2.7 Hz, 1H), 7.51 (td, J=8.6, 2.7 Hz, 1H), 3.79-3.73 (m, 4H), 3.70 (s, 2H), 2.52 (s, 4H).

Embodiment Example 6—Synthesis of 2-((4-methyl-piperazin-1-yl)methyl)indolo[2,1-b]quinazoline-6,12-dione (1f)

Step (1) is as specified in Embodiment Example 1.

Step (2): Synthesis of 2-methyl-indole[2,1-b]quinazoline-6,12-dione (4b)

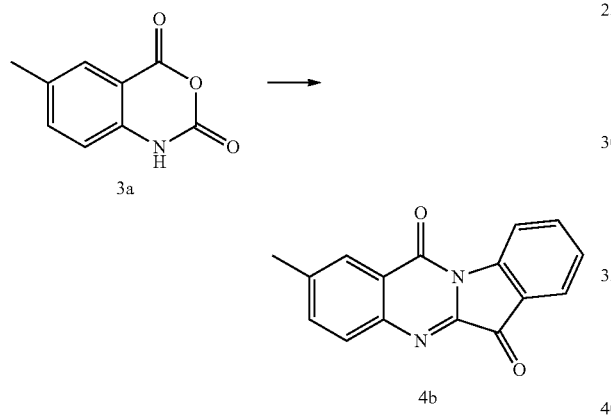

A mixture of Compound 3a (1.7 g, 9.6 mmol), isatin (1.4 g, 9.6 mmol) and triethylamine (2.7 ml, 19.2 mmol) was suspended in dry toluene (18 ml) and heated at 110° C. for 4 hours. Once the reaction solution had cooled to room temperature, the resulting yellow solid was filtered and washed three times will 2 ml of ethyl acetate to obtain a yellow solid compound (4b) (0.5 g, 20%).

Characterization Data:

$^1$H NMR (400 MHz, CDCl$_3$) δ 8.65 (d, J=8.1 Hz, 1H), 8.25 (s, 1H), 7.94 (dd, J=7.8, 5.0 Hz, 2H), 7.85-7.75 (m, 1H), 7.71-7.64 (m, 1H), 7.44 (t, J=7.5 Hz, 1H), 2.58 (s, 3H).

Step (3): Synthesis of 2-methyl-indole[2,1-b]quinazoline-6,12-dione (5b)

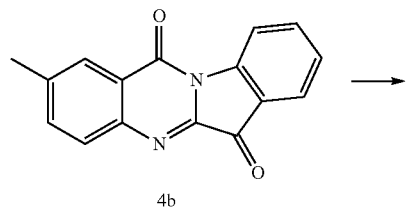

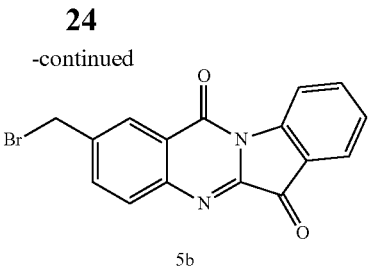

A mixture of NBS (381 mg, 2.14 mmol) and AIBN (29 mg, 0.18 mmol) was added in three batches to a dichloromethane solution (5 ml) containing Compound 4b (262 mg, 1.0 mmol) at a temperature of 80° C. under the protection of nitrogen gas. Once the reaction solution had cooled to room temperature, washing was performed with a salt solution and drying was performed over anhydrous sodium sulfate to obtain a concentrated yellow product (5b) (245 mg, 91%).

Step (4): Synthesis of 2-((4-methyl-piperazin-1-yl)methyl)indolo[2,1-b]quinazoline-6,12-dione (1f)

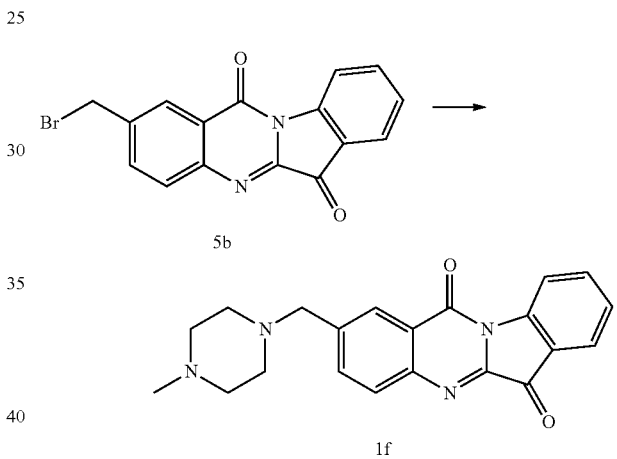

Compound 5b (220 mg, 0.61 mmol), N-methylpiperazine (116 mg, 1.616 mmol), potassium iodide (10 mg) and triethylamine (0.5 ml) were stirred in a 5 ml solution of DMF at room temperature for 2 hours. Once TLC confirmed that the reaction was complete, 50 ml of water was added and three consecutive extractions were performed using 10 ml of ethyl acetate, after which the organic phase was washed three times with water and drying was performed over anhydrous sodium sulfate. The concentrated yellow solid obtained was subjected to separation using a silica gel column to obtain a yellow compound (1f) (120 mg, 55%).

Characterization Data:

$^1$H NMR (400 MHz, CDCl3) δ 8.66 (d, J=8.1 Hz, 1H), 8.39 (s, 1H), 8.01 (d, J=8.3 Hz, 1H), 7.94 (d, J=7.5 Hz, 1H), 7.89 (dd, J=8.2, 1.7 Hz, 1H), 7.82 (t, J=7.8 Hz, 1H), 7.45 (t, J=7.5 Hz, 1H), 3.71 (s, 2H), 2.71-2.41 (m, 8H), 2.33 (s, 3H).

Embodiment Example 7—Detection of IDO Inhibitory Activity

During the construction of a plasmid containing a human IDO gene, expressed in *Escherichia coli*, extraction and purification were performed according to the method reported by Littlejohn, et al. (Takikawa O, Kuroiwa T, Yamazaki F, et al. J. Biol. Chem. 1988, 263, 2041-2048). The IDO inhibitory activity with respect to each compound was detected using the methods described in the literature. 50 mM potassium phosphate buffer (pH 6.5), 40 mM vitamin C, 400 μg/ml catalase, 20 μM methylene blue and IDO enzyme were mixed together in a 96-well plate. The substrate L-tryptophan and the sample to be tested were then added to the aforementioned mixture. The reaction was carried out for 60 minutes at 37° C., after which the reaction was terminated by adding 30% (w/v) trichloroacetic acid. The 96-well plate was heated to 65° C. for 15 minutes to complete the conversion from formylkynurenine to kynurenine, and centrifugation was performed with 6000 g for 5 minutes. 100 μl of supernatant was removed from each well and transferred to a new 96-well plate, after which an acetic acid solution of 2% (w/v) p-(dimethylamino)benzaldehyde was added, and the yellow color produced as a result of the resulting reaction with kynurenine was observable at 490 nm in a microplate reader; the experimental results are shown in Table 1.

Embodiment Example 8—Determining Whether or not an Inhibitor is Reversible

A series of different enzymatic concentrations were tested, given a fixed concentration of inhibitor, and the resulting reaction rates were measured. A graph of reaction rate versus enzyme concentration (v-[E]) was plotted and it was possible to determine whether or not the inhibitor was reversible based on the characteristics of the resulting curve.

Reaction Conditions: 50 mM potassium phosphate buffer (pH 6.5), 40 mM vitamin C, 400 μg/ml catalase, 20 μM methylene blue and 300 mM of the substrate L-tryptophan or simultaneously 100 mM of inhibitor were added to a 500 μl the reaction system, after which the mixture was maintained at 37° C. for 5 minutes, after which varying volumes of an IDO enzyme were added to the aforementioned mixture and the resulting reaction was allowed to proceed for 30 minutes at 37° C., and 200 μL of 30% (w/v) trichloroacetic acid was added to terminate the reaction; the reaction system was heated to 65° C. for 15 minutes to complete the conversion of formylkynurenine to kynurenine, after which centrifugation was performed for 10 minutes at 12,000 rpm, the supernatant was removed and mixed with an equal volume of 2% (w/v) p-dimethylaminobenzaldehyde acetic acid solution, and measurements were performed using a plate reader at a wavelength of 490 nm. v-[E] was plotted and the experimental results are shown in Table 1.

Embodiment Example 9—Determining Inhibitor Type and Ki Value Measurement 50 mM potassium phosphate buffer (pH 6.5), 40 mM vitamin C, 400 μg/ml catalase, 20 μM methylene blue and 100, 250 or 300 mM of the substrate L-tryptophan were added to a 500 μl the reaction system and varying concentrations of the compound were added to each reaction system for a given single substrate concentration, after which the mixture was maintained at 37° C. for 5 minutes, after which 10 μl of IDO (approximately 20 nM) was added to the aforementioned mixture and the resulting reaction was allowed to proceed for 30 minutes at 37° C., and 200 μL of 30% (w/v) trichloroacetic acid was added to terminate the reaction; the reaction system was heated to 65° C. in a water bath for 15 minutes to complete the conversion of formylkynurenine to kynurenine, after which centrifugation was performed for 10 minutes at 12,000 rpm, the supernatant was removed and mixed with an equal volume of 2% (w/v) p-dimethylaminobenzaldehyde acetic acid solution, and measurements were performed using a plate reader at a wavelength of 490 nm. A Dixon plot (1/v-[I]) was used to determine the type of inhibitor constituted by the compound and a plot of S/v-[I] was created to obtain an inhibitor Ki value; the experimental results are shown in Table 1.

Embodiment Example 10—Measurement of Median Effective Inhibition Concentration $IC_{50}$ 50 mM potassium phosphate buffer (pH 6.5), 40 mM vitamin C, 400 μg/ml catalase, 20 μM methylene blue, 150 mM of the substrate L-tryptophan and inhibitor were mixed together. Mixtures containing 100, 200, 400, 600, 800, 1000 or 1200 μM of inhibitor were heated to 37° C. for 5 minutes and an IDO enzyme was then added to the above mixtures. The reaction was allowed to proceed at 37° C. for 30 minutes, after which 200 μL of 30% (w/v) trichloroacetic acid was added to terminate the reaction; the reaction system was heated to 65° C. for 15 minutes to complete the conversion of formylkynurenine to kynurenine, after which centrifugation was performed for 10 minutes at 12,000 rpm, 200 μL of the supernatant was removed and mixed with an equal volume of 2% (w/v) p-dimethylaminobenzaldehyde acetic acid solution, and the yellow color produced as a result of the resulting reaction with kynurenine was observable at 490 nm in a microplate reader; the results thus obtained were fed into $IC_{50}$ calculation software to obtain inhibitor $IC_{50}$ values; and the experimental results are shown in Table 1.

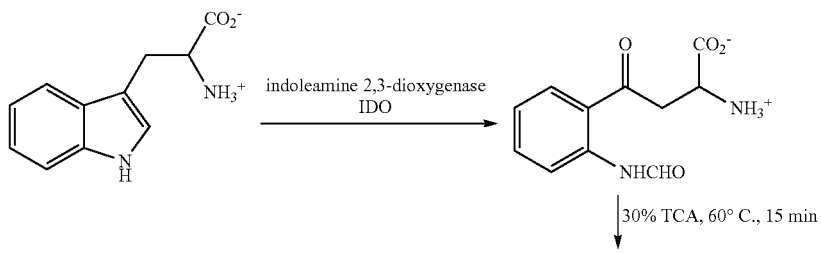

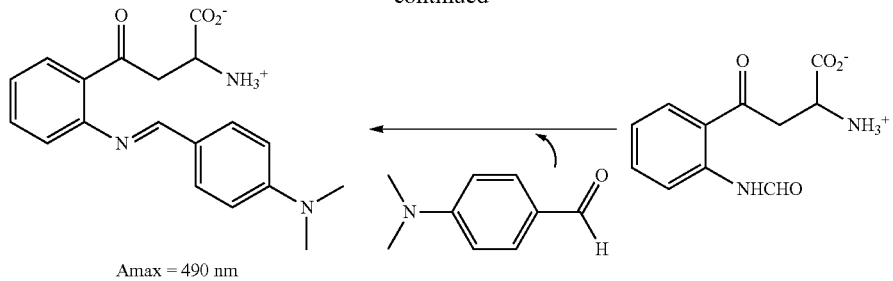

λmax = 490 nm

Embodiment Example 11—Measurement of Median Effective Inhibition Concentration $IC_{50}$ (Cells)

The liposome Lipofectamin 2000 was used to transfect HEK 293 cells with the pcDNA3.1-hIDO plasmid. When measuring the inhibition activity at the cellular level, the HEK293 cell culture medium corresponded to high glucose DMEM, containing 50 U/mL penicillin, 50 U/mL streptomycin and 10% FBS, and culturing was performed at 37° C. under 5% $CO_2$. Twenty four hours following cell transfection with the plasmid, the test drug was added and incubation was performed, after which the supernatant was transferred to another 96-well plate and 10 μL 30% (w/v) trichloroacetic acid was added and the mixture was heated to 65° C. for 15 minutes to complete the conversion of formylkynurenine to kynurenine, after which centrifugation was performed for 10 minutes at 12,000 rpm, an equal volume of 2% (w/v) p-dimethylaminobenzaldehyde acetic acid solution was mixed in, and the absorbance was measured at 490 nm using a plate reader; the experimental results are shown in Table 1.

Measurements of the IDO inhibitory activity of the compounds obtained in Embodiment Examples 1-6 were performed using the methods given in Embodiment Examples 7-11 above, and the IDO inhibitor 1-methyl-tryptophan (1-MT, commercially available), which is currently commonly used in both in vivo and in vitro experiments, was used as a control; the results are shown in Table 1.

TABLE 1

IDO inhibitory activity of N-benzyl tryptanthrin derivatives (I) synthesized in the above embodiment examples

| Compound | Inhibition Type | $K_i$ (μM) (in vitro) | $IC_{50}$ (μM) (Cell) | $IC_{50}$ (μM) |
|---|---|---|---|---|
| | Competitive | 34 | 380 | 18.4 |
| Embodiment Example 1 | Anticompetitive | 0.31 | 0.11 | $1.01 \times 10^{-3}$ |
| Embodiment Example 2 | Anticompetitive | 7.21 | 1.88 | 0.64 |
| Embodiment Example 3 | Noncompetitive | 4.12 | 0.68 | $7.38 \times 10^{-2}$ |
| Embodiment Example 4 | Anticompetitive | 2.64 | 0.50 | $2.24 \times 10^{-2}$ |
| Embodiment Example 5 | Anticompetitive | 0.47 | 0.40 | $1.21 \times 10^{-3}$ |
| Embodiment Example 6 | Anticompetitive | 5.97 | 2.52 | 0.97 |

Example 12—T-Cell Proliferation Assay 12.1. Isolation of Spleen Lymphocytes (Performed in Accordance with the Lymphocyte Separation Medium Instructions):
1. Two mice were sacrificed by cervical dislocation and spleens were removed on a sterile table and placed into a 6 cm plate containing an RP1640 culture medium for later use.
2. A 100 μm mesh was placed in a 50 mL centrifuge tube and each spleen was cut into smaller pieces using scissors, milled on top of the sieve and a small amount of RP1640 was added for preservation purposes.
3. A lymphocyte separation medium equivalent to twice the volume of the resulting slurry was then added.
4. Centrifugation was performed at 800 g for 20 minutes, after which three distinct layers were visible, with the middle layer showing a slight yellowish tint.
5. Cells in the middle layer were removed and an RP1640 culture medium was added to perform a reverse wash. Cells were then centrifuged at 250 g for 10 minutes at room temperature, and the cells were collected.
6. The culture medium was aspirated off and cells were resuspended in the RP1640 medium, after which a cell count was performed.

12.2. LLC (Lewis Lung Carcinoma) Cell Treatment:
1. A medium (high glucose DMEM, 10% FBS) was aspirated off and washing was performed 1-2 times using PBS;
2. 0.25% trypsin was added to initiate digestion;
3. The trypsin was aspirated off and a culture medium was added, after which cells were pipetted off and transferred to a 1.5 mL centrifuge tube;
4. Centrifugation followed by aspiration of the supernatant was performed, and cells were resuspended in 1 mL of the DMEM culture medium;
5. Mitomycin C (final concentration: 25 μg/mL) was added, the mixture was pipetted up and down until homogeneous, and the mixture was placed in a 37° C. bath for 30 minutes;
6. Washing was performed 3 times with RP1640, the cells were counted and the sample was set aside.

12.3. Experimental Procedure
1. Treated LLC cells ($2 \times 10^4$ cells/well; stimulator cells) and spleen lymphocytes ($10^5$ cells/well; reaction cells) were added to a 96-well plate, after which RP1640 (10% FBS was added to bring the volume to 200 μL;
2. Grouping was performed and 50 μM IDO inhibitor was added for the administration group, after which samples were placed in a 37° C., 95% RH, 5% $CO_2$ incubator and cultured for 72 hours;
3. A WST-1 reagent kit was used to measure T-cell proliferation, and absorbance values at a wavelength of 450 nm were measured using a plate reader;
4. Calculation of the T Lymphocyte Proliferation Rate:

T lymphocyte proliferation rate (%)=[administration group well(T lymphocytes+LLC cells+IDO inhibitor)OD value−control well(T lymphocytes+LLC cells)OD value]/control well(T lymphocytes+LLC cells)OD value×100%

12.4. Experimental Results

TABLE 2

Stimulation of T-cell proliferation by N-benzyl tryptanthrin derivatives synthesized in the aforementioned embodiment examples

| Embodiment Example 1 | Embodiment Example 2 | Embodiment Example 3 | Embodiment Example 4 | Embodiment Example 5 | Embodiment Example 6 | T-Cell Proliferation Rate |
|---|---|---|---|---|---|---|
| 4.88% | 38.48 | 40.64 | 41.24 | 50.27 | 39.40 | 13.84 |

Embodiment Example 13—The Anti-Tumor Effect of 8-fluoro-2-((4-methyl-piperazin-1-yl)methyl)indolo[2,1-b]quinazoline-6,12-dione (Embodiment Example 4)

1. Establishment of LLC Lewis Tumor Model: Healthy female C57BL/6 mice weighing 20±1 g and purchased from the Shanghai Slyke Experimental Animal Center were raised in an SPF grade laboratory. Sterile saline was used to suspend Lewis lung carcinoma cells at a concentration of $1 \times 10^7$/mL. Cells were subcutaneously inoculated in the underarm region of mice under sterile operational conditions, with 0.2 mL being inoculated in each animal.

2. Experimental Grouping and Prophylactic Administration: Mice were randomly divided into five groups of 10 animals. The control group was given an equivalent volume of 0.5% sodium carboxymethyl cellulose via gavage; 1-methyl-tryptophan (1-MT) was administered at concentrations of 150 mg/kg in the high dosage group and 75 mg/kg in the low dosage group via gavage; 8-fluoro-2-((4-methyl-piperazin-1-yl)methyl)indolo[2,1-b]quinazoline-6,12-dione was administered at concentrations of 150 mg/kg in the High Dosage Group and 75 mg/kg in the Low Dosage Group via gavage. Tumor inoculation was performed following 7 days of continuous administration, after which administration was continued for 21 days and tumor growth was observed. Tumor length along the major axis (a) and minor axis (b) was measured starting on the day of tumor inoculation and every other day thereafter, with tumor volume=$ab^2/2$. On the day after administration was discontinued, mice were scarified via cervical dislocation and the tumors were removed, weighed and preserved in liquid nitrogen.

3. Treatment Results for Prophylactic Administration: Following prophylactic administration lasting one week followed by continued administration after inoculation, mice which were administered with 8-fluoro-2-((4-methyl-piperazin-1-yl)methyl)indolo[2,1-b]quinazoline-6,12-dione showed significantly inhibited Lewis lung carcinoma tumor growth in vivo; no significant tumor formation was observed in the high dosage group 20 days after administration was started, while tumor formation was noted just 11 days following the start of administration in the control group; mice in the 1-MT group showed tumor formation 13 days after the start of administration. On a tumor volume basis, the tumor inhibition rates observed for the 8-fluoro-2-((4-methyl-piperazin-1-yl)methyl)indolo[2,1-b] quinazoline-6,12-dione and 1-MT high dosage groups were 62.15% and 32.35% respectively, while tumor inhibition rates were 46.62% and 27.00% in the low dosage groups. On a tumor weight basis, the tumor inhibition rates observed for the 8-fluoro-2-((4-methyl-piperazin-1-yl)methyl)indolo[2,1-b]quinazoline-6,12-dione and 1-MT high dosage groups were 57.8% and 28.2% respectively. Animals administered with 8-fluoro-2-((4-methyl-piperazin-1-yl) methyl) indolo [2,1-b] quinazoline-6,12-dione exhibited normal weight, a shiny coat and a more flexible response.

4. Experimental Grouping and Post-Inoculation Administration: Mice were randomly divided into four groups of 10 animals 48 hours after tumor inoculation was performed. An initial dose was administered once the tumor diameter had reached 5 mm. Animals in the control group were administered with an equal volume of 0.5% CMC (sodium carboxymethyl cellulose) via gavage; animals in the 1-MT group were administered with a dose of 200 mg/kg, via gavage; animals in the 8-fluoro-2-((4-methyl-piperazin-1-yl)methyl)indolo[2,1-b]quinazoline-6,12-dione group were administered a dose of 200 mg/kg, via gavage; animals in the paclitaxel group were administered with a dose of 100 mg/kg via intravenous injection, once per week; animals in the 8-fluoro-2-((4-methyl-piperazin-1-yl)methyl)indolo[2,1-b]quinolin oxazoline-6,12-dione+paclitaxel group were administered with 200 mg/kg 8-fluoro-2-((4-methyl-piperazin-1-yl)methyl)indolo[2,1-b]quinazoline-6,12-dione and 100 mg/kg paclitaxel (caudal vein intravenous injection) continuously for two weeks. The tumor length along the major axis (a) and minor axis (b) was measured starting on the day of administration and every other day thereafter, with tumor volume=$ab^2/2$. On the day after administration was discontinued, mice were scarified via cervical dislocation, tumors were removed, weighed and preserved in liquid nitrogen.

5. Treatment Results for Post-Inoculation Administration: After animals were subjected to two weeks of continuous administration of 200 mg/kg of 8-fluoro-2-((4-methyl-piperazin-1-yl)methyl)indolo[2,1-b]quinazoline-6,12-dione or 1-MT via gavage, in vivo Lewis lung carcinoma tumor growth showed significant inhibition compared to the control group, and inhibition of tumor growth was more pronounced in the 8-fluoro-2-((4-methyl-piperazin-1-yl) methyl)indolo[2,1-b]quinazoline-6,12-dione group versus the 1-MT group. On a tumor volume basis, the tumor inhibition rates observed for the 8-fluoro-2-((4-methyl-piperazin-1-yl)methyl)indolo[2,1-b]quinazoline-6,12-dione, 1-MT, paclitaxel and 8-fluoro-2-((4-methyl-piperazin-1-yl) methyl)indolo[2,1-b]quinazoline-6,12-dione paclitaxel groups were 23.38%, 15.68%, 51.45% and 72.48%, respectively. As a chemotherapy drug commonly used in clinical practice, paclitaxel generally produced inhibition of tumor growth, but the drug also produced stronger toxic side effects; during the course of the experiment, mice were observed as losing weight, losing their fur and showing less movement in general. On the other hand, although administration of only 8-fluoro-2-((4-methyl-piperazin-1-yl) methyl)indolo[2,1-b]quinazoline-6,12-dione did not result in complete disappearance of the tumor, a more significant inhibition of the tumor was observed and mice thus treated exhibited a normal weight, a shiny coat and a more flexible response.

Comparative Example—The Preparation of 2-methyl-indole[2,1-b]quinazoline-6,12-dione and Activity Testing Step (1) is as specified in Embodiment Example 1.

Step (2): Synthesis of 2-methyl-indole[2,1-b]quinazoline-6,12-dione (4b)

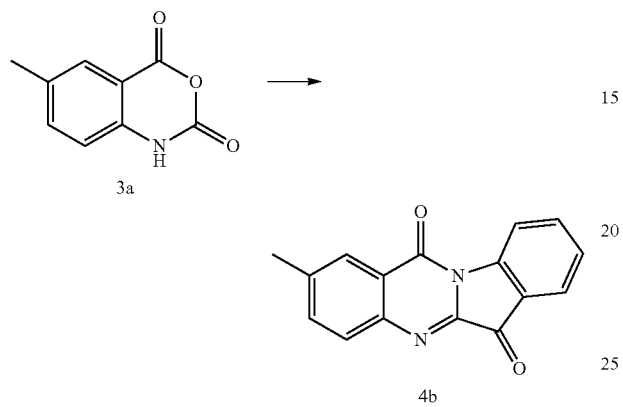

A mixture of Compound 3a (1.7 g, 9.6 mmol), isatin (1.4 g, 9.6 mmol) and triethylamine (2.7 ml, 19.2 mmol) was suspended in dry toluene (18 ml) and heated at 110° C. for 4 hours. Once the reaction solution had cooled to room temperature, the resulting yellow solid was filtered and washed three times with 2 ml of ethyl acetate to obtain a yellow solid compound (4b) (0.5 g, 20%).
Characterization Data:
$^1$H NMR (400 MHz, CDCl$_3$) δ 8.65 (d, J=8.1 Hz, 1H), 8.25 (s, 1H), 7.94 (dd, J=7.8, 5.0 Hz, 2H), 7.85-7.75 (m, 1H), 7.71-7.64 (m, 1H), 7.44 (t, J=7.5 Hz, 1H), 2.58 (s, 3H).

Using the measurement method described in Embodiment Example 9-11 to measure the activity of the compound obtained in the Comparative Example yielded an IDO inhibitory activity in vitro IC$_{50}$ of 997.25 μM, while the Ki and in vivo IC$_{50}$ were not measured.

As the experimental data in Table 1 demonstrates, the compound pertaining to the present application exhibits an exceptionally good IDO inhibitory activity relative to currently available conventional IDO inhibitors, as well as compounds with similar structures. More specifically, compared with the existing conventional IDO inhibitor 1-MT, the in vitro and intracellular IC$_{50}$ values obtained for the compound constituted by the present application are lower by 1-3 orders of magnitude, indicating that the compound constituted by the present application produces an excellent IDO inhibitory activity.

It is worth noting that there is a very significant improvement in the compound constituted by the present application versus other compounds with highly similar structures (such as the compound given in the Comparative Example) in terms of inhibitory activity. The inhibitory activity is still greatly increased even compared to certain IDO inhibitors which similarly feature active groups in their structure. Given the link between the compound structure and activity typically observed in this field, the difference observed between the compound constituted by the present application and similar structures is a highly exceptional phenomenon. This indicates that the compound constituted by the present application constitutes an extremely unique type of structure, and the biological activity thereof is surprising.

All publications mentioned in the present invention are incorporated into the references as if each individual publication was cited as a reference. It should also be understood that after reading the instructions provided in the present invention, a person skilled in the art should be able to make various changes or modifications to the invention, and these equivalent forms also fall within the scope of the claims which are included in this application.

The invention claimed is:
1. An N-benzyl tryptanthrin derivative, which is characterized in that said derivative has the structure as shown in Formula 1 below:

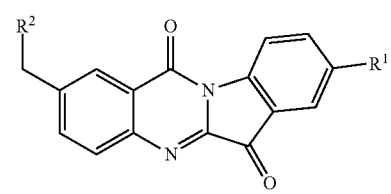

1 where
R$^1$ corresponds to hydrogen or fluorine;
R$^2$ corresponds to —NR$^3$R$^4$;
R$^3$ and R$^4$ are each independently selected from the following set: H, substituted or unsubstituted C1-C4 alkyl groups, substituted or unsubstituted C2-C4 alkenyl groups, substituted or unsubstituted C2-C4 alkynyl groups, and substituted or unsubstituted C3-C6 cycloalkyl groups;
or R$^3$ and R$^4$ together with an adjacent nitrogen atom form a substituted or unsubstituted 5-7 membered heterocyclic ring, where said ring includes 1-2 nitrogen atoms as well as 0-2 heteroatoms selected from the following set: O and S;
substitution refers to cases in which one or more hydrogen atoms present on a given group are substituted by a substituent selected from the group consisting of: C1-C4 alkyl groups, C1-C4 haloalkyl groups, amino-protecting groups and halogens.
2. The N-benzyl tryptanthrin derivative as claimed in claim 1, characterized in that R$^3$ and R$^4$ are each independently selected from: C1-C4 alkyl groups; or, R$^3$ and R$^4$ together with an adjacent nitrogen atom form a substituted or unsubstituted 5-6 membered saturated ring, where said 5-6 membered saturated ring includes 1 or 2 nitrogen atoms as well as an optional heteroatom selected from the following set: O.
3. The N-benzyl tryptanthrin derivative as claimed in claim 1, characterized in that R$^2$ is a substituted or unsubstituted group selected from the group consisting of:

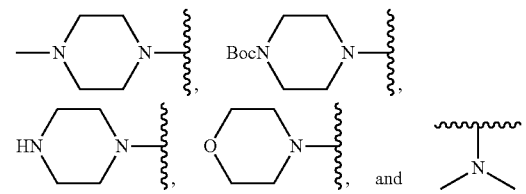

where "~" indicates a connection site;
substitution refers to cases in which one or more hydrogen atoms present on a given group are substituted by a substituent selected from the following set: C1-C4 alkyl groups and halogens.

4. An N-benzyl tryptanthrin derivative, characterized in that the structure of said derivative is as given below:

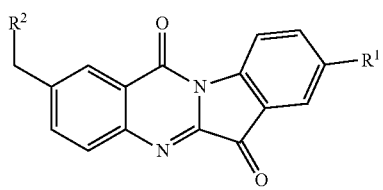

1 wherein R¹=H or F; and
R²=

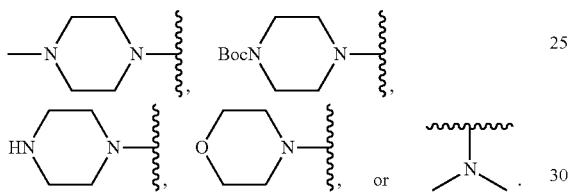

5. The N-benzyl tryptanthrin derivative as claimed in claim 4, characterized in that said derivative is a compound selected from the group consisting of:

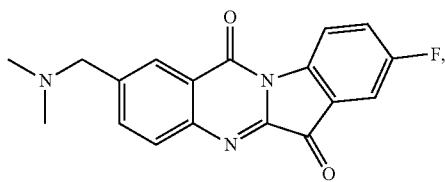

1a

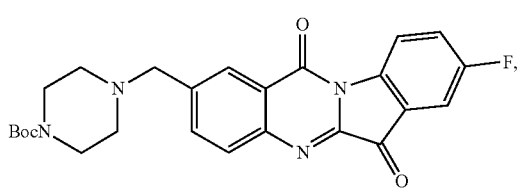

1b

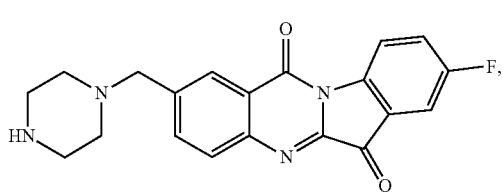

1c

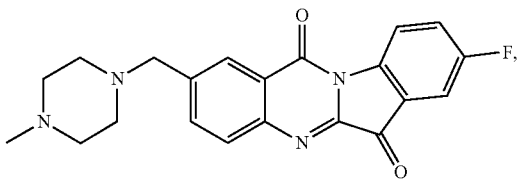

1d

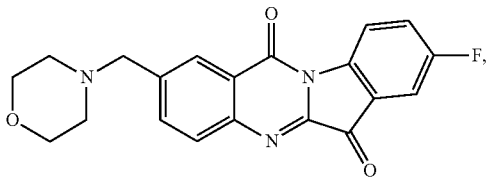

1e

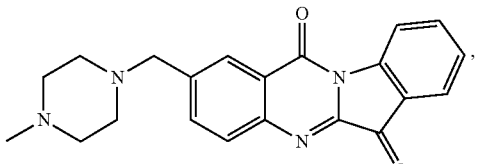

1f

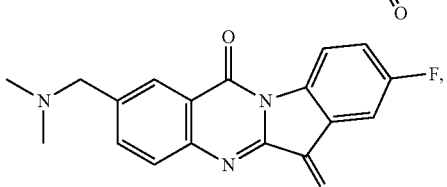

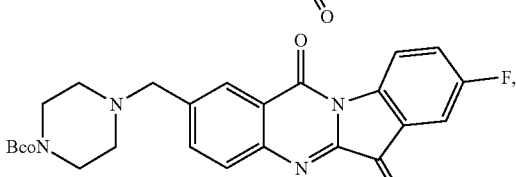

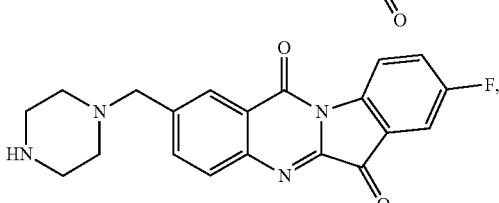

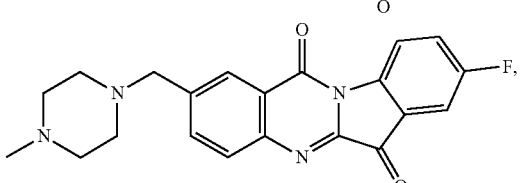

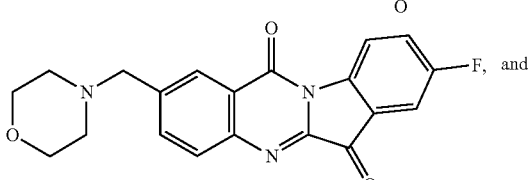

, and

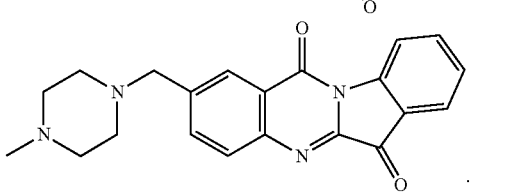

.

6. A method for the preparation of the N-benzyl tryptanthrin derivative as claimed in claim 1 comprising reacting the compound given in Formula 5 (2-bromomethyl-tryptanthrin) with R²H in an inert solvent in the presence of triethylamine to obtain the compound shown in Formula 1, where R¹ and R² are as defined in claim 1.

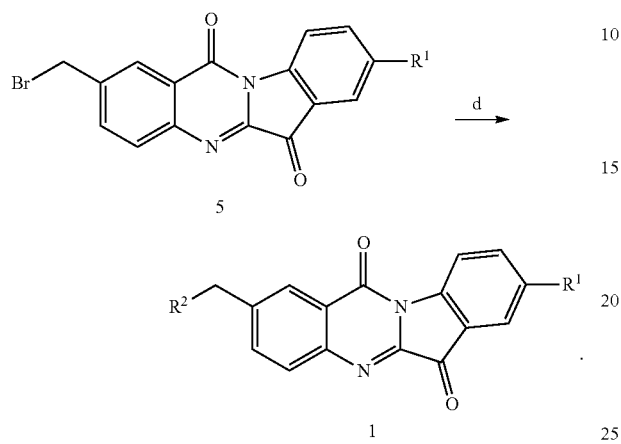

7. The method according to claim 6, wherein said method is preceded by the following step;

reacting the compound given in Formula 4 with a bromination agent in an inert solvent to obtain the compound given in Formula 5.

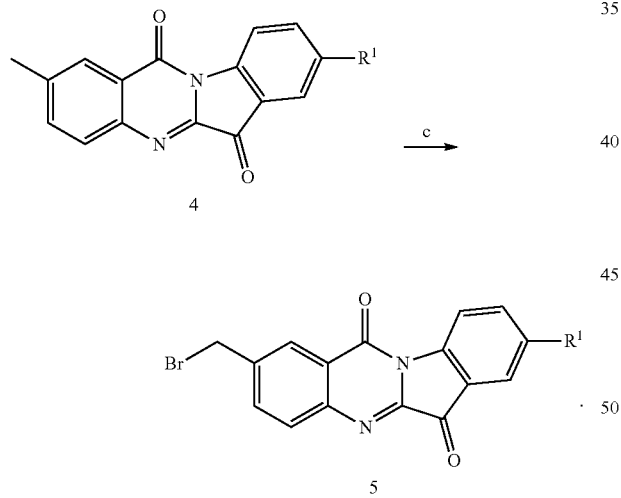

8. A method for the preparation of an N-benzyl tryptanthrin derivative according to claim 4 comprising,

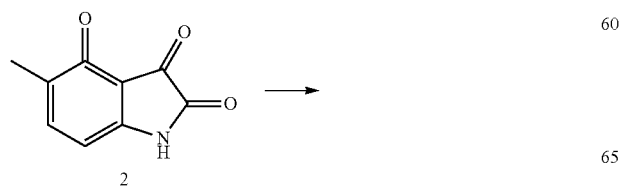

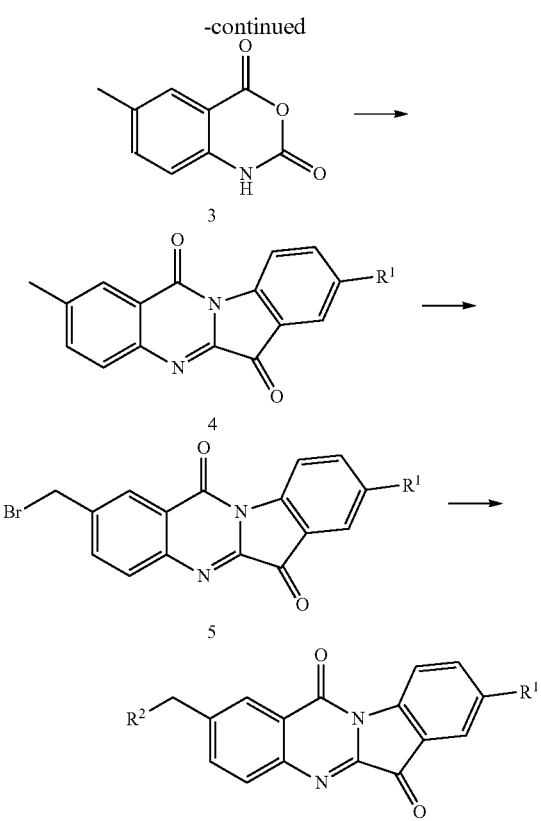

(1) Synthesis of Methylisatoic Anhydride

Suspending 5-methylisatin in dry dichloromethane and adding meta-chloroperoxybenzoic acid batchwise at 0° C., then stirring for 1.5-2.5 hours at room temperature; confirming that the reaction is complete via TLC, filtering off the white solid produced in the reaction and washing three times with ethyl acetate to obtain 5-methylisatoic anhydride; wherein the molar ratio of 5-methylisatin and meta-chloroperoxybenzoic acid is (0.5-1):1; and (2) Synthesis of 2-Methyltryptanthrin Suspending a mixture of methylisatoic anhydride, 5-fluoroisatin and triethylamine in dry toluene, then heating for 3.5-4.5 hours at a temperature of 100-120° C. and distilling off the solvent under reduced pressure; dissolving the resulting yellow solid in dichloromethane and adding ethyl acetate, then filtering the resulting yellow solid and washing with ethyl acetate three times to obtain 2-methyltryptanthrin; wherein the molar ratio of methylisatoic anhydride, 5-fluoroisatin and triethylamine is (0.2-0.5):(0.2-0.5):1; and (3) Synthesis of 2-bromomethyl-tryptanthrin Dissolving the 2-methyltryptanthrin obtained in Step (2) in dry dichloromethane at 75-85° C. under the protection of nitrogen gas, then adding in a mixture of N-bromosuccinimide (NBS)- and azobisisobutyronitrile (AIBN) batchwise; heating the reaction solution at 75° C. for 15-17 hours and confirming that the reaction is comple via TLC; cooling the reaction solution to room temperature, washing the reaction solution with a salt solution and drying over anhydrous sodium sulfate; and concentrating the organic phase to obtain a yellow product wherein the molar ratio of 2-methyltryptanthrin, NBS and AIBN is 1:1:(0.005-0.02); and (4) Synthesis of N-Benzyltryptanthrin Stirring together 2-bromomethyl-tryptanthrin, an aliphatic amine and triethylamine at room temperature in dry dimethylformamide (DMF) for 1.5-2.5 hours, verifying that the reaction is complete via TLC, adding 50 ml of water and performing three sequential extractions using 10 ml of dichloromethane; followed by subjecting the entire volume of dichloromethane obtained to three washes with water and then drying over anhydrous sodium sulfate; separating the concentrated yellow solid obtained using silica gel to obtain a yellow-colored N-benzyl tryptanthrin derivative; wherein the molar ratio of 2-bromomethyl-tryptanthrin, the aliphatic amine and triethylamine is 1:(1-2):(2-5).

9. A pharmaceutical composition, characterized in that it includes: (i) the compound according to claim 1 or a pharmaceutically acceptable salt thereof; and (ii) a pharmaceutically acceptable carrier.

10. A compound of Formula 1 according to claim 1 or a pharmaceutically acceptable salt thereof, wherein said compound is an IDO inhibitor.

11. A method for inhibiting IDO activity in vitro, in which a compound according to claim 1 or a pharmaceutically acceptable salt thereof is brought into contact with an inhibition target in an amount which produces effective inhibition.

12. A method for the preparation of a pharmaceutical composition wherein a compound according to claim 1 or a pharmaceutically acceptable salt thereof is mixed with a pharmaceutically acceptable carrier in a therapeutically effective amount to create a pharmaceutical composition.

13. A method for treating a disease associated with a disorder in the tryptophan metabolism comprising administering a compound according to claim 1 or a pharmaceutically acceptable salt thereof in a therapeutically effective amount to a subject in need of treatment.

14. The method according to claim 13 wherein the disease is selected from one or more of, depression, anxiety, AIDS, autoimmune diseases, mental disorders, Lyme disease infections, streptococcal infections, neurodegenerative disorders, cancer, and ocular diseases.

15. The method according to claim 14, wherein the cancer is T-cell leukemia or colon cancer.

* * * * *